US011254983B2

(12) United States Patent
Dehlinger et al.

(10) Patent No.: US 11,254,983 B2
(45) Date of Patent: Feb. 22, 2022

(54) PHOTONIC SUPERLATTICE-BASED DEVICES AND COMPOSITIONS FOR USE IN LUMINESCENT IMAGING, AND METHODS OF USING THE SAME

(71) Applicant: Illumina, Inc., San Diego, CA (US)

(72) Inventors: Dietrich Dehlinger, San Francisco, CA (US); Cheng Frank Zhong, San Francisco, CA (US); Juraj Topolancik, Redwood, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 16/949,821

(22) Filed: Nov. 16, 2020

(65) Prior Publication Data

US 2021/0238673 A1 Aug. 5, 2021

Related U.S. Application Data

(63) Continuation of application No. 16/656,317, filed on Oct. 17, 2019, now Pat. No. 10,837,057, which is a
(Continued)

(51) Int. Cl.
*C12Q 1/6874* (2018.01)
*G01N 21/64* (2006.01)
(Continued)

(52) U.S. Cl.
CPC ...... *C12Q 1/6874* (2013.01); *B01L 3/502715* (2013.01); *G01N 21/6428* (2013.01);
(Continued)

(58) Field of Classification Search
CPC ............. C12Q 1/6874; B01L 3/502715; B01L 3/5027; B01L 2300/0654;
(Continued)

(56) References Cited

U.S. PATENT DOCUMENTS 4,349,796 A 9/1982 Chin et al.
5,026,148 A 6/1991 Wen et al.
(Continued)

FOREIGN PATENT DOCUMENTS

CN 101057132 A 10/2007
CN 102305774 A 1/2012
(Continued)

OTHER PUBLICATIONS

International Search Report and Written Opinion for PCT Application No. PCT/US2017/023900, dated Aug. 24, 2017, 26 pages.
(Continued)

*Primary Examiner* — Blake C Riddick
(74) *Attorney, Agent, or Firm* — Brake Hughes Bellermann LLP

(57) ABSTRACT

Under one aspect, a device is provided for use in luminescent imaging. The device can include a photonic superlattice including a first material, the first material having a first refractive index. The first material can include first and second major surfaces and first and second pluralities of features defined through at least one of the first and second major surfaces, the features of the first plurality differing in at least one characteristic from the features of the second plurality. The photonic superlattice can support propagation of a first wavelength and a second wavelength approximately at a first angle out of the photonic superlattice, the first and second wavelengths being separated from one another by a first non-propagating wavelength that does not selectively propagate at the first angle out of the photonic superlattice.

20 Claims, 9 Drawing Sheets

Related U.S. Application Data continuation of application No. 16/035,208, filed on Jul. 13, 2018, now Pat. No. 10,472,675, which is a continuation of application No. 15/468,024, filed on Mar. 23, 2017, now Pat. No. 10,059,992.

(60) Provisional application No. 62/312,704, filed on Mar. 24, 2016.

(51) Int. Cl.
| | |
|---|---|
| G02B 5/20 | (2006.01) |
| B01L 3/00 | (2006.01) |
| G02B 21/00 | (2006.01) |
| G02B 21/18 | (2006.01) |
| G02B 21/36 | (2006.01) |
| G01N 21/77 | (2006.01) |
| G01N 21/03 | (2006.01) |
| G01N 21/25 | (2006.01) |

(52) U.S. Cl.
CPC ..... *G01N 21/6452* (2013.01); *G01N 21/6454* (2013.01); *G01N 21/7743* (2013.01); *G02B 5/20* (2013.01); *G02B 21/0076* (2013.01); *G02B 21/18* (2013.01); *G02B 21/361* (2013.01); *B01L 3/5027* (2013.01); *B01L 2300/0654* (2013.01); *B01L 2300/0819* (2013.01); *B01L 2300/0864* (2013.01); *B01L 2300/168* (2013.01); *G01N 21/0303* (2013.01); *G01N 21/253* (2013.01); *G01N 21/6458* (2013.01); *G01N 2021/6421* (2013.01)

(58) Field of Classification Search
CPC ..... B01L 2300/0819; B01L 2300/0864; B01L 2300/168; G01N 21/6428; G01N 21/6452; G01N 21/7743; G01N 21/0303; G01N 21/253; G01N 21/6458; G01N 2021/6421; G02B 21/0076; G02B 21/18; G02B 21/361
See application file for complete search history.

(56) References Cited

U.S. PATENT DOCUMENTS

| | | | |
|---|---|---|---|
| 7,057,026 | B2 | 6/2006 | Barnes et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,768,640 | B2 | 8/2010 | Cunningham et al. |
| 8,344,333 | B2 | 1/2013 | Lu et al. |
| 8,636,955 | B2 | 1/2014 | Chakravarty et al. |
| 2006/0119853 | A1 | 6/2006 | Baumberg et al. |
| 2008/0108082 | A1 | 5/2008 | Rank et al. |
| 2008/0230716 | A1 | 9/2008 | Tysoe et al. |
| 2009/0321261 | A1 | 12/2009 | Vlahovic et al. |
| 2011/0059865 | A1 | 3/2011 | Smith et al. |
| 2012/0007000 | A1 | 1/2012 | Lu et al. |
| 2012/0014837 | A1 | 1/2012 | Fehr et al. |
| 2012/0229891 | A1 | 9/2012 | Liu et al. |
| 2013/0005606 | A1 | 1/2013 | Chakravarty et al. |
| 2013/0079232 | A1 | 3/2013 | Kain et al. |
| 2014/0079923 | A1 | 3/2014 | George et al. |
| 2014/0243224 | A1 | 8/2014 | Barnard et al. |
| 2014/0326302 | A1 | 11/2014 | Arakawa et al. |
| 2015/0338345 | A1 | 11/2015 | Lakowicz et al. |

FOREIGN PATENT DOCUMENTS

| | | |
|---|---|---|
| CN | 102628805 A | 8/2012 |
| CN | 102243165 B | 7/2013 |
| CN | 103323428 A | 9/2013 |
| CN | 103398974 A | 11/2013 |
| CN | 104624258 A | 5/2015 |
| EP | 2154515 A1 | 2/2010 |
| KR | 20130117301 A | 10/2013 |
| WO | 9106678 A1 | 5/1991 |
| WO | 2004018497 A2 | 3/2004 |
| WO | 2007123744 A2 | 11/2007 |

OTHER PUBLICATIONS

Bentley et al.; "Accurate Whole Human Genome Sequencing Using Reversible Terminator Chemistry", Nature, vol. 456, 53-59, Nov. 2008.

Chaudhery, et al., "Nanostructured Surfaces and Detection Instrumentation for Photonic Crystal Enhanced Fluorescence", Sensors vol. 13 (5), 5561-5584, 2013.

Estrada, et al., "Small volume excitation and enhancement of dye fluorescence on a 2D photonic crystal surface", Optics Express vol. 18, No. 4, 3693-3699, Feb. 2010.

Kaji, "Fabrication of two-dimensional Ta2O5 photonic crystal slabs with ultra-low background emission toward highly sensitive fluorescence spectroscopy", Optics Express, 19(2), 1422-1428, Jan. 2011.

Neff, et al., "A Photonic Crystal Superlattice based on Triangular Lattice", Optics Express, 13(8), pp. 3166-3173, Mar. 15, 2005.

Pokhriyal, et al., "Photonic crystal enhanced fluorescence using a quartz substrate to reduce limits of detection", Optics Express, 18(24), 24793-24808. Nov. 2010.

Pokhriyal, A , et al., "Multicolor fluorescence enhancement from a photonics crystal surface", Pokhriyal, A. , et al., "Multicolor fluorescence enhancement from a photonics crystal surface", Appl. Phys. Lett. 97, Sep. 2010, 121108-121108.

Zhen, et al., "Enabling enhanced emission and low-threshold lasing of organic molecules using special Fano resonances of macroscopic photonic crystals", 13711-13716, 2013.

U.S. Appl. No. 16/656,317, filed Oct. 17, 2019.

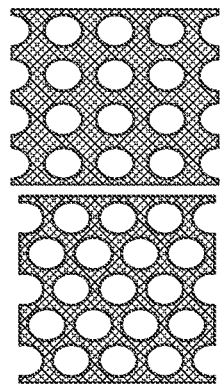
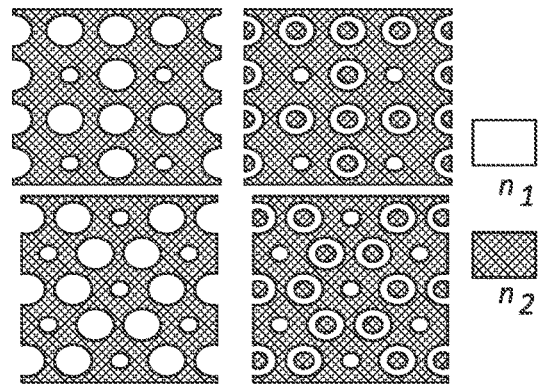
FIG. 1A  
FIG. 1B
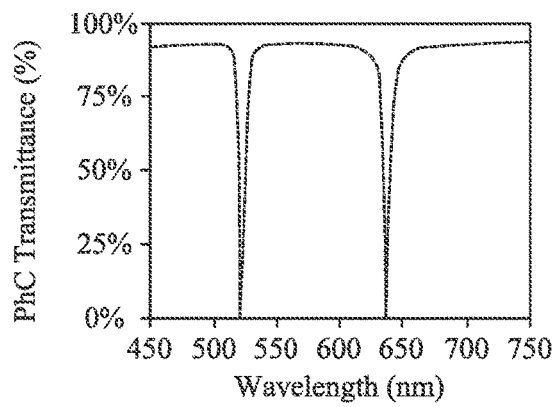
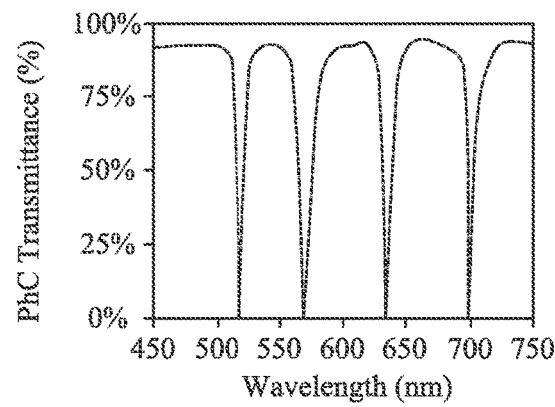
FIG. 1C  
FIG. 1D

FIG. 6A
Resin 1
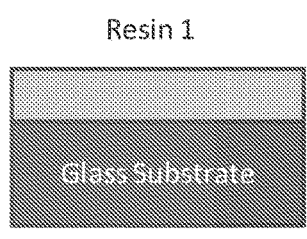
FIG. 6B
Nanoimprint 1
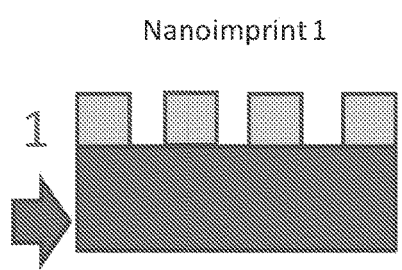
FIG. 6C
High Index Coating 1
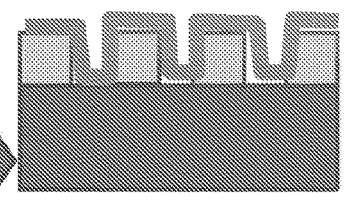
Resin 2
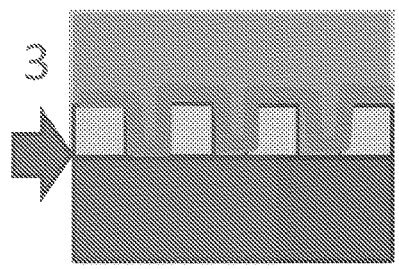
FIG. 6D
Nanoimprint 2
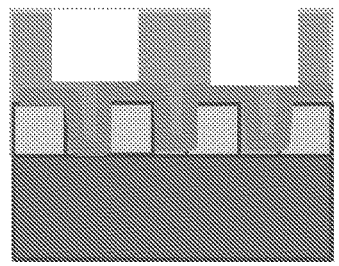
FIG. 6E FIG. 7A
Dielectric 1
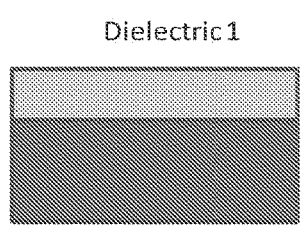
FIG. 7B
Litho and RIE 1
FIG. 7C
High Index Coating
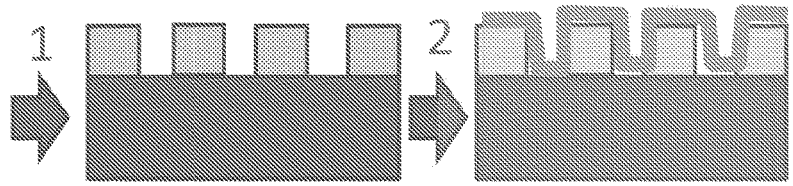
FIG. 7D
Dielectric 2
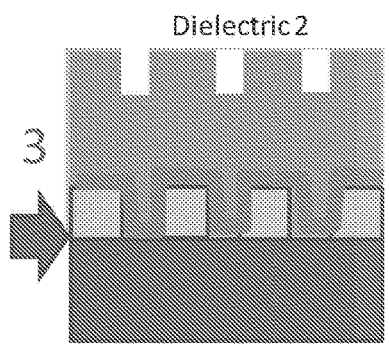
FIG. 7E
CMP
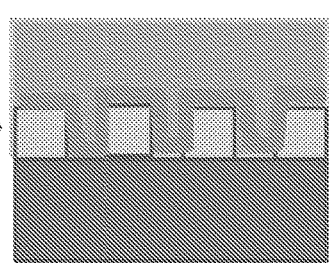
FIG. 7F
Litho and RIE 2
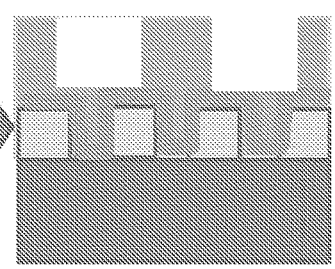
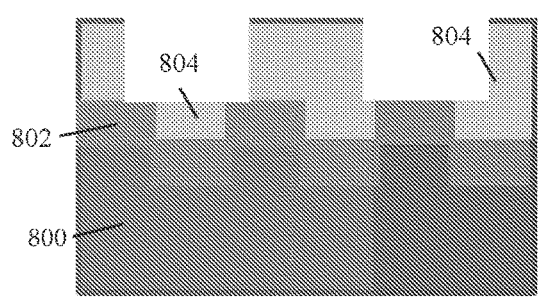
FIG. 8A
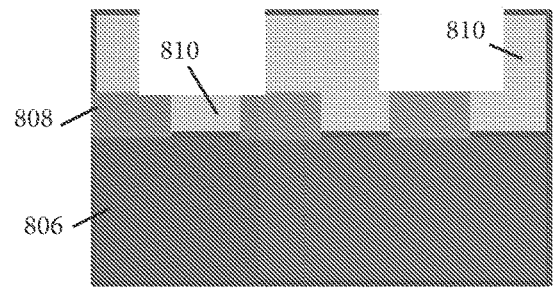
FIG. 8B

PHOTONIC SUPERLATTICE-BASED DEVICES AND COMPOSITIONS FOR USE IN LUMINESCENT IMAGING, AND METHODS OF USING THE SAME

CROSS-REFERENCE TO RELATED APPLICATIONS

The present application is a continuation of, and claims the benefit of the filing date of, U.S. application Ser. No. 16/656,317, filed Oct. 17, 2019, and entitled PHOTONIC SUPERLATTICE-BASED DEVICES AND COMPOSITIONS FOR USE IN LUMINESCENT IMAGING, AND METHODS OF USING THE SAME, now U.S. Pat. No. 10,837,057, which is a continuation of, and claims the benefit of the filing date of, U.S. application Ser. No. 16/035,208, filed Jul. 13, 2018, and entitled PHOTONIC SUPERLATTICE-BASED DEVICES AND COMPOSITIONS FOR USE IN LUMINESCENT IMAGING, AND METHODS OF USING THE SAME, now U.S. Pat. No. 10,472,675, which is a continuation of, and claims the benefit of the filing date of, U.S. application Ser. No. 15/468,024, filed Mar. 23, 2017, and entitled PHOTONIC SUPERLATTICE-BASED DEVICES AND COMPOSITIONS FOR USE IN LUMINESCENT IMAGING, AND METHODS OF USING THE SAME, now U.S. Pat. No. 10,059,992, which claims the benefit of the filing date of U.S. Provisional Appl. No. 62/312,704, filed Mar. 24, 2016. The contents of all applications mentioned above are incorporated herein by reference.

FIELD

This application generally relates to luminescent imaging.

BACKGROUND

Certain state-of-the-art sequencing tools developed by industry leaders rely on various "sequencing by synthesis (SBS)" chemistries to determine a polynucleotide sequence, such as a DNA or RNA sequence. Sequencing can involve using luminescent imaging, such as a fluorescent microscopy system, to identify nucleotides or localized clusters of identical nucleotides by emission wavelength of their respective fluorescent markers. Although some SBS chemistries under development can require as few as a single dye, multiple fluorescent dyes (up to four) are generally used in commercial systems so as to uniquely identify the nucleotides in a polynucleotide, such as A, G, C, and T nucleotides in DNA.

SUMMARY

Embodiments of the present invention provide photonic superlattice-based devices and compositions for use in luminescent imaging, and methods of using the same.

Under one aspect, a device is provided for use in luminescent imaging. The device can include a photonic superlattice including a first material, the first material having a first refractive index. The first material can include first and second major surfaces and first and second pluralities of features defined through at least one of the first and second major surfaces, the features of the first plurality differing in at least one characteristic from the features of the second plurality. The photonic superlattice can support propagation of a first wavelength and a second wavelength approximately at a first angle out of the photonic superlattice, the first and second wavelengths being separated from one another by a first non-propagating wavelength that does not selectively propagate at the first angle out of the photonic superlattice. The device further can include a second material having a second refractive index that is different than the first refractive index. The second material can be disposed within, between, or over the first and second pluralities of features and can include first and second luminophores. The device further can include a first optical component disposed over one of the first and second major surfaces of the first material. The first optical component can receive luminescence emitted by the first luminophore at the first wavelength approximately at the first angle, and can receive luminescence emitted by the second luminophore at the second wavelength approximately at the first angle.

Optionally, the photonic superlattice further includes a third material having a third refractive index that is different than the first and second refractive indices. The third material can be disposed over at least one of the first and second pluralities of features, and the second material can be disposed over the third material.

Additionally, or alternatively, the first and second pluralities of features respectively optionally can include first and second pluralities of wells.

Additionally, or alternatively, the second material optionally further can include third and fourth luminophores. The photonic superlattice further can support propagation of a third wavelength and a fourth wavelength approximately at the first angle out of the photonic superlattice, the third and fourth wavelengths can be separated from one another by a second non-propagating wavelength that does not selectively propagate at the first angle. The optical component can receive luminescence emitted by the third luminophore at the third wavelength approximately at the first angle, and can receive luminescence emitted by the fourth luminophore at the fourth wavelength approximately at the first angle. Optionally, the first luminophore is coupled to a first nucleic acid, the second luminophore is coupled to a second nucleic acid that is different than the first nucleic acid, the third luminophore is coupled to a third nucleic acid that is different than the first and second nucleic acids, and the fourth luminophore is coupled to a fourth nucleic acid that is different than the first, second, and third nucleic acids.

Additionally, or alternatively, the first luminophore optionally is coupled to a first nucleic acid, and the second luminophore optionally is coupled to a second nucleic acid that is different than the first nucleic acid.

Additionally, or alternatively, the at least one characteristic optionally includes shape, size, or distribution.

Additionally, or alternatively, the device optionally further includes a second optical component configured so as to transmit radiation to the photonic superlattice approximately at a second angle. The first luminophore can emit the first wavelength responsive to the radiation transmitted by the second optical component, and the second luminophore can emit the second wavelength responsive to the radiation transmitted by the second optical component. Optionally, the second angle is approximately the same as the first angle. Additionally, or alternatively, the first and second angles optionally each can be approximately normal to the first and second major surfaces. Optionally, the second angle is approximately orthogonal to the first angle. Optionally, the first and second optical components include the same optical component. Optionally, the first optical component is disposed over the first major surface of the first material, and wherein the second optical component is disposed over the second major surface of the first material.

Additionally, or alternatively, the device optionally can include a broadband excitation source configured to generate the radiation transmitted to the photonic superlattice by the second optical component. Optionally, the broadband excitation source includes a light emitting diode.

Additionally, or alternatively, the device optionally includes at least one microfluidic feature in contact with the photonic superlattice and configured to provide a flow of one or more analytes to the first and second pluralities of features.

Additionally, or alternatively, the first optical component optionally includes an image sensor configured to image the received first and second wavelengths.

Additionally, or alternatively, the first material optionally can include a polymer or a glass. Additionally, or alternatively, the second material optionally can include a fluid or a gel.

Additionally, or alternatively, the first angle optionally is approximately normal to the first and second major surfaces.

Additionally, or alternatively, the first luminophore optionally is coupled to a first polynucleotide to be sequenced, and the second luminophore optionally is coupled to a second polynucleotide to be sequenced. Optionally, the first polynucleotide is coupled to a feature of the first plurality of features, and the second polynucleotide is coupled to a feature of the second plurality of features. Additionally, or alternatively, the device optionally further can include a first polymerase adding a first nucleic acid to a third polynucleotide that is complementary to and coupled to the first polynucleotide. The first nucleic acid can be coupled to the first luminophore. The device optionally further can include a second polymerase adding a second nucleic acid to a fourth polynucleotide that is complementary to and coupled to the second polynucleotide. The second nucleic acid can be coupled to the second luminophore. Additionally, or alternatively, the device further can include a channel flowing a first liquid including the first and second nucleic acids and the first and second polymerases into, between, or over the first and second pluralities of features.

Under another aspect, a method is provided for use in luminescent imaging. The method can include providing a photonic superlattice including a first material, the first material having a first refractive index. The first material can include first and second major surfaces and first and second pluralities of features defined through at least one of the first and second major surfaces. The features of the first plurality can differ in at least one characteristic from the features of the second plurality. The photonic superlattice can support propagation of a first wavelength and a second wavelength approximately at a first angle out of the photonic superlattice. The first and second wavelengths can be separated from one another by a first non-propagating wavelength that does not selectively propagate at the first angle out of the photonic superlattice. The method further can include providing a second material having a second refractive index that is different than the first refractive index. The second material can be disposed within, between, or over the first and second pluralities of features and can include first and second luminophores. The method further can include providing a first optical component disposed over one of the first and second major surfaces of the first material. The method further can include receiving by the first optical component luminescence emitted by the first luminophore at the first wavelength approximately at the first angle; and receiving by the first optical component luminescence emitted by the second luminophore at the second wavelength approximately at the first angle.

Optionally, the first and second pluralities of features respectively include first and second pluralities of wells.

Additionally, or alternatively, the photonic superlattice optionally further includes a third material having a third refractive index that is different than the first and second refractive indices. The third material can be disposed over at least one of the first and second pluralities of features, and the second material can be disposed over the third material.

Additionally, or alternatively, the second material optionally further can include third and fourth luminophores. The photonic superlattice further can support propagation of a third wavelength and a fourth wavelength approximately at the first angle out of the photonic superlattice. The third and fourth wavelengths can be different than each of the first and second wavelengths and can be separated from one another by a second non-propagating wavelength that does not selectively propagate at the first angle. The method further can include receiving by the first optical component luminescence emitted by the third luminophore at the third wavelength approximately at the first angle; and receiving by the first optical component luminescence emitted by the fourth luminophore at the fourth wavelength approximately at the first angle. Optionally, the first luminophore is coupled to a first nucleic acid, the second luminophore is coupled to a second nucleic acid that is different than the first nucleic acid, the third luminophore is coupled to a third nucleic acid that is different than the first and second nucleic acids, and the fourth luminophore is coupled to a fourth nucleic acid that is different than the first, second, and third nucleic acids.

Additionally, or alternatively, the first luminophore optionally is coupled to a first nucleic acid, and the second luminophore optionally is coupled to a second nucleic acid that is different than the first nucleic acid.

Additionally, or alternatively, the at least one characteristic optionally includes shape, size, or distribution.

Additionally, or alternatively, the method optionally further can include, by a second optical component, transmitting radiation to the photonic superlattice approximately at a second angle. The first luminophore can emit the first wavelength responsive to the radiation transmitted by the second optical component, and the second luminophore can emit the second wavelength responsive to the radiation transmitted by the second optical component. Optionally, the second angle is approximately the same as the first angle. Additionally, or alternatively, the first and second angles each can be approximately normal to the first and second major surfaces. Optionally, the second angle is approximately orthogonal to the first angle. Optionally, the first and second optical components include the same optical component. Optionally, the first optical component is disposed over the first major surface of the first material, and the second optical component is disposed over the second major surface of the first material.

Additionally, or alternatively, the method optionally further can include generating by a broadband radiation source the radiation transmitted to the photonic superlattice by the second optical component. Optionally, the broadband excitation source includes a light emitting diode.

Additionally, or alternatively, the method optionally further can include flowing one or more analytes into, between, or over the first and second pluralities of features by at least one microfluidic feature in contact with the photonic superlattice.

Additionally, or alternatively, the first optical component optionally includes an image sensor imaging the received first and second wavelengths.

Additionally, or alternatively, the first material optionally includes a polymer or a glass. Additionally, or alternatively, the second material optionally includes a fluid or a gel.

Additionally, or alternatively, the first angle optionally is approximately normal to the first and second major surfaces.

Additionally, or alternatively, the method optionally further can include coupling the first luminophore to a first polynucleotide to be sequenced; and coupling the second luminophore to a second polynucleotide to be sequenced. Optionally, the method further can include coupling the first polynucleotide to a feature of the first plurality of features; and coupling the second polynucleotide to a feature of the second plurality of features. Additionally, or alternatively, the method further can include, by a first polymerase, adding a first nucleic acid to a third polynucleotide that is complementary to and coupled to the first polynucleotide. The first nucleic acid can be coupled to the first luminophore. The method optionally further can include, by a second polymerase, adding a second nucleic acid to a fourth polynucleotide that is complementary to and coupled to the second polynucleotide. The second nucleic acid can be coupled to the second luminophore. Additionally, or alternatively, the method optionally further can include flowing a first liquid including the first and second nucleic acids and the first and second polymerases into, between, or over the first and second pluralities of features. Additionally, or alternatively, the method optionally further can include, after receiving by the first optical component the luminescence emitted by the first and second luminophores, respectively decoupling the first and second luminophores from the first and second polynucleotides to be sequenced. Optionally, the method further can include, after respectively decoupling the first and second luminophores from the first and second polynucleotides to be sequenced, flowing a second liquid including third and fourth nucleic acids and third and fourth polymerases into, between, or over the first and second pluralities of features. The third nucleic acid can be coupled to the first luminophore, and the fourth nucleic acid can be coupled to the second luminophore. The method optionally further can include, by the third polymerase, adding the third nucleic acid or the fourth nucleic acid to the third polynucleotide; or by the fourth polymerase, adding the third nucleic acid or the fourth nucleic acid to the fourth polynucleotide.

Under another aspect, a composition is provided. The composition can include a photonic superlattice; and a first nucleic acid in contact with the photonic superlattice.

Optionally, the photonic superlattice includes a first material having a first refractive index. The first material can include first and second major surfaces and first and second pluralities of features defined through at least one of the first and second major surfaces. The features of the first plurality can differ in at least one characteristic from the features of the second plurality. The photonic superlattice can support propagation of a first wavelength and a second wavelength approximately at a first angle out of the photonic superlattice. The first and second wavelengths can be separated from one another by a first non-propagating wavelength that does not selectively propagate at the first angle out of the photonic superlattice. The composition further can include a second material having a second refractive index that is different than the first refractive index. The second material can be disposed within, between, or over the first and second pluralities of features and can include first and second luminophores. The first luminophore can be coupled to the first nucleic acid, and the second luminophore can be coupled to a second nucleic acid that is different than the first nucleic acid. Optionally, the first and second pluralities of features respectively include first and second pluralities of wells. Additionally, or alternatively, the first luminophore can emit luminescence at the first wavelength, and the second luminophore can emit luminescence at the second wavelength. Optionally, the luminescence emitted by the first luminophore approximately is at the first angle, and the luminescence emitted by the second luminophore approximately is at the first angle. Additionally, or alternatively, the first angle is approximately normal to the first and second major surfaces. Additionally, or alternatively, the photonic superlattice optionally further includes a third material having a third refractive index that is different than the first and second refractive indices. The third material can be disposed over at least one of the first and second pluralities of features, and the second material can be disposed over the third material.

Additionally, or alternatively, the second material optionally further can include third and fourth luminophores. The photonic superlattice further can support propagation of a third wavelength and a fourth wavelength approximately at the first angle out of the photonic superlattice, the third and fourth wavelengths can be separated from one another by a second non-propagating wavelength that does not selectively propagate at the first angle. The third luminophore can emit luminescence at the third wavelength approximately at the first angle, and the fourth luminophore can emit luminescence at the fourth wavelength approximately at the first angle. Optionally, the first luminophore is coupled to a first nucleic acid, the second luminophore is coupled to a second nucleic acid that is different than the first nucleic acid, the third luminophore is coupled to a third nucleic acid that is different than the first and second nucleic acids, and the fourth luminophore is coupled to a fourth nucleic acid that is different than the first, second, and third nucleic acids.

Additionally, or alternatively, optionally the first luminophore is coupled to a first nucleic acid, and optionally the second luminophore is coupled to a second nucleic acid that is different than the first nucleic acid.

Additionally, or alternatively, the at least one characteristic optionally includes shape, size, or distribution.

Additionally, or alternatively, the first luminophore optionally can emit the first wavelength responsive to radiation approximately at a second angle, and the second luminophore can emit the second wavelength responsive to radiation approximately at the second angle. Optionally, the second angle is approximately the same as the first angle. Additionally, or alternatively, the first and second angles optionally each are approximately normal to the first and second major surfaces. Optionally, the second angle is approximately orthogonal to the first angle.

Additionally, or alternatively, the first material optionally includes a polymer or a glass. Additionally, or alternatively, the second material optionally includes a fluid or a gel. Additionally, or alternatively, the first luminophore optionally is coupled to a first polynucleotide to be sequenced, and the second luminophore is coupled to a second polynucleotide to be sequenced. Optionally, the first polynucleotide is coupled to a feature of the first plurality of features, and the second polynucleotide is coupled to a feature of the second plurality of features. Additionally, or alternatively, the composition optionally further can include a first polymerase adding a first nucleic acid to a third polynucleotide that is complementary to and coupled to the first polynucleotide.

The first nucleic acid can be coupled to the first luminophore. The composition optionally further can include a second polymerase adding a second nucleic acid to a fourth polynucleotide that is complementary to and coupled to the second polynucleotide. The second nucleic acid can be coupled to the second luminophore. Optionally, the composition further can include a channel flowing a first liquid including the first and second nucleic acids and the first and second polymerases into, between, or over the first and second pluralities of features.

Optionally, the photonic superlattice further is in contact with a microfluidic feature. Optionally, the microfluidic feature includes a nanowell or a microfluidic channel.

Additionally, or alternatively, the composition optionally further can include a luminophore that can emit luminescence at a wavelength. Optionally, the luminescence emitted by the luminophore is at an angle to the first and second major surfaces. Optionally, the angle is approximately normal to the first and second major surfaces.

Additionally, or alternatively, the photonic superlattice optionally includes a first material having a first refractive index. The first material can include first and second major surfaces and a plurality of features defined through at least one of the first and second major surfaces. The composition further can include a second material having a second refractive index that is different than the first refractive index; and a third material having a third refractive index that is different than the first and second refractive indices. The third material can be disposed over at least some features of the plurality of features, and the second material can be disposed over the third material. Optionally, the first material includes a polymer or a glass. Additionally, or alternatively, the second material optionally includes a fluid or a gel.

Additionally, or alternatively, the photonic superlattice optionally can support propagation of a first wavelength and a second wavelength approximately at a first angle out of the photonic superlattice. The first and second wavelengths can be separated from one another by a first non-propagating wavelength that does not selectively propagate at the first angle out of the photonic superlattice. Optionally, the photonic superlattice further can support propagation of a third wavelength and a fourth wavelength approximately at the first angle out of the photonic superlattice. The third and fourth wavelengths can be separated from one another by a second non-propagating wavelength that does not selectively propagate at the first angle the photonic superlattice.

Additionally, or alternatively, the composition optionally further can include a luminophore coupled to the nucleic acid. Optionally, the luminophore can emit luminescence at an angle and at a wavelength responsive to radiation approximately at the angle. Additionally, or alternatively, the nucleic acid optionally is coupled to a first polynucleotide to be sequenced. Optionally, the first polynucleotide is coupled to a feature of the photonic superlattice. Additionally, or alternatively, the composition optionally further can include a polymerase adding the nucleic acid to a second polynucleotide that is complementary to and coupled to the first polynucleotide.

Under another aspect, a composition is provided. The composition can include a photonic superlattice; and a microfluidic feature in contact with the photonic superlattice.

Optionally, the microfluidic feature includes a nanowell or a microfluidic channel. Additionally, or alternatively, the photonic superlattice optionally includes a first material having a first refractive index. The first material can include first and second major surfaces and first and second pluralities of features defined through at least one of the first and second major surfaces. The features of the first plurality can differ in at least one characteristic from the features of the second plurality. The photonic superlattice can support propagation of a first wavelength and a second wavelength approximately at a first angle out of the photonic superlattice. The first and second wavelengths can be separated from one another by a first non-propagating wavelength that does not selectively propagate at the first angle out of the photonic superlattice. The composition further can include a second material having a second refractive index that is different than the first refractive index. The second material can be disposed within, between, or over the first and second pluralities of features and can include first and second luminophores. The first luminophore can be coupled to the first nucleic acid, and the second luminophore can be coupled to a second nucleic acid that is different than the first nucleic acid.

Optionally, the first and second pluralities of features respectively include first and second pluralities of wells.

Additionally, or alternatively, the first luminophore optionally can emit luminescence at the first wavelength, and the second luminophore optionally can emit luminescence at the second wavelength. Optionally, the luminescence emitted by the first luminophore is approximately at the first angle, and the luminescence emitted by the second luminophore is approximately at the first angle. Optionally, the first angle is approximately normal to the first and second major surfaces.

Additionally, or alternatively, the photonic superlattice optionally further includes a third material having a third refractive index that is different than the first and second refractive indices. The third material can be disposed over at least one of the first and second pluralities of features, and the second material can be disposed over the third material.

Additionally, or alternatively, the second material optionally further can include third and fourth luminophores. The photonic superlattice further can support propagation of a third wavelength and a fourth wavelength approximately at the first angle out of the photonic superlattice. The third and fourth wavelengths can be separated from one another by a second non-propagating wavelength that does not selectively propagate at the first angle out of the photonic superlattice. The third luminophore can emit luminescence at the third wavelength approximately at the first angle, and the fourth luminophore can emit luminescence at the fourth wavelength approximately at the first angle. Optionally, the first luminophore is coupled to a first nucleic acid, the second luminophore is coupled to a second nucleic acid that is different than the first nucleic acid, the third luminophore is coupled to a third nucleic acid that is different than the first and second nucleic acids, and the fourth luminophore is coupled to a fourth nucleic acid that is different than the first, second, and third nucleic acids.

Additionally, or alternatively, the first luminophore optionally is coupled to a first nucleic acid, and the second luminophore optionally is coupled to a second nucleic acid that is different than the first nucleic acid.

Additionally, or alternatively, the at least one characteristic optionally includes shape, size, or distribution.

Additionally, or alternatively, the first luminophore optionally can emit the first wavelength responsive to radiation approximately at a second angle, and the second luminophore optionally can emit the second wavelength responsive to radiation approximately at the second angle. Optionally, the second angle is approximately the same as the first angle. Additionally, or alternatively, the first and second angles optionally each are approximately normal to the first and second major surfaces. Optionally, the second angle is approximately orthogonal to the first angle.

Additionally, or alternatively, the first material optionally includes a polymer or a glass. Additionally, or alternatively, the second material optionally includes a fluid or a gel.

Additionally, or alternatively, the first luminophore is coupled to a first polynucleotide to be sequenced, and the second luminophore is coupled to a second polynucleotide to be sequenced. Optionally, the first polynucleotide is coupled to a feature of the first plurality of features, and wherein the second polynucleotide is coupled to a feature of the second plurality of features.

Additionally, or alternatively, the composition optionally further can include a first polymerase adding a first nucleic acid to a third polynucleotide that is complementary to and coupled to the first polynucleotide. The first nucleic acid can be coupled to the first luminophore. Optionally, the composition further can include a second polymerase adding a second nucleic acid to a fourth polynucleotide that is complementary to and coupled to the second polynucleotide. The second nucleic acid can be coupled to the second luminophore. Optionally, the composition further can include a channel flowing a first liquid including the first and second nucleic acids and the first and second polymerases into, between, or over the first and second pluralities of features.

Optionally, the composition further can include a luminophore that can emit luminescence at a wavelength. Optionally, the luminescence emitted by the luminophore is at an angle to the first and second major surfaces. Optionally, the angle is approximately normal to the first and second major surfaces.

Additionally, or alternatively, the photonic superlattice optionally includes a first material having a first refractive index. The first material can include first and second major surfaces and a plurality of features defined through at least one of the first and second major surfaces. The composition further can include a second material having a second refractive index that is different than the first refractive index; and a third material having a third refractive index that is different than the first and second refractive indices. The third material can be disposed over the plurality of features, and the second material can be disposed over the third material. Optionally, the first material includes a polymer or a glass. Additionally, or alternatively, the second material optionally includes a fluid or a gel.

Additionally, or alternatively, the photonic superlattice optionally can support propagation of a first wavelength and a second wavelength approximately at an angle out of the photonic superlattice. The first and second wavelengths can be separated from one another by a first non-propagating wavelength that does not selectively propagate at the angle out of the photonic superlattice. Optionally, the photonic superlattice further can support propagation of a third wavelength and a fourth wavelength approximately at the angle out of the photonic superlattice. The third and fourth wavelengths can be separated from one another by a second non-propagating wavelength that does not selectively propagate at the angle out of the photonic superlattice.

Additionally, or alternatively, the composition optionally further can include a luminophore coupled to the nucleic acid. Optionally, the luminophore can emit luminescence at a first angle and at a wavelength responsive to radiation approximately at a second angle.

Additionally, or alternatively, the nucleic acid optionally is coupled to a first polynucleotide to be sequenced. Optionally, the first polynucleotide is coupled to a feature of the photonic superlattice. Additionally, or alternatively, the composition optionally further can include a polymerase adding the nucleic acid to a second polynucleotide that is complementary to and coupled to the first polynucleotide.

Under another aspect, a composition is provided. The composition can include a photonic superlattice; and a pattern of analyte sites in contact with the photonic superlattice. A first luminophore can be present at a first subset of analyte sites in the pattern and a second luminophore can be present at a second subset of analyte sites in the pattern. The photonic superlattice is tuned to selectively propagate into the photonic superlattice a first wavelength that excites the first luminophore and a second wavelength that excites the second luminophore. The first and second wavelengths are separated by a non-propagating wavelength that does not selectively propagate into the photonic superlattice.

Optionally, the photonic superlattice is tuned to create field enhancements for the first and second wavelengths at the analyte sites.

Additionally, or alternatively, a third luminophore optionally is present at a third subset of analyte sites in the pattern. The photonic superlattice can be further tuned to selectively propagate into the photonic superlattice a third wavelength that excites the third luminophore. Optionally, a fourth luminophore is present at a fourth subset of analyte sites in the pattern. The photonic superlattice can be further tuned to selectively propagate into the photonic superlattice a fourth wavelength that excites the fourth luminophore. Optionally, the first, second, third and fourth wavelengths are separated by respective wavelengths that do not selectively propagate into the photonic superlattice.

Additionally, or alternatively, the analyte optionally includes nucleic acid.

Under another aspect, a method is provided. The method can include providing a device including a photonic superlattice; and a pattern of analyte sites in contact with the photonic superlattice. A first luminophore can be present at a first subset of analyte sites in the pattern and a second luminophore is present at a second subset of analyte sites in the pattern. The method also can include contacting the device with radiation that includes a first wavelength and a second wavelength. The photonic superlattice selectively propagates into the photonic superlattice the first wavelength to excite the first luminophore and selectively propagates into the photonic superlattice the second wavelength to excite the second luminophore. The first and second wavelengths can be separated by a non-propagating wavelength that does not selectively propagate into the photonic superlattice. The method further can include detecting emission from the first and second luminophores, thereby detecting the first and second analytes.

Optionally, the superlattice is tuned to create field enhancements for the first and second wavelengths at the analyte sites.

Additionally, or alternatively, a third luminophore optionally is present at a third subset of analyte sites in the pattern. The photonic superlattice can be further tuned to selectively propagate into the photonic superlattice a third wavelength that excites the third luminophore. Optionally, a fourth luminophore is present at a fourth subset of analyte sites in the pattern. The photonic superlattice can be further tuned to selectively propagate into the photonic superlattice a fourth wavelength that excites the fourth luminophore. Optionally, the first, second, third and fourth wavelengths are separated by respective wavelengths that do not selectively propagate into the photonic superlattice.

Additionally, or alternatively, the analyte optionally includes nucleic acid.

BRIEF DESCRIPTION OF THE DRAWINGS

FIG. 1A schematically illustrates plan views of square and hexagonal lattice photonic crystals (PhCs), FIG. 1B schematically illustrates plan views of exemplary compositions including PhC superlattices provided herein, FIG. 1C schematically illustrates a plot of a simulated transmission spectrum at normal incidence showing resonances of an exemplary PhC lattice, and FIG. 1D schematically illustrates a plot of a simulated transmission spectrum at normal incidence showing resonances of an exemplary composition including a PhC superlattice provided herein.

FIGS. 6A-6E illustrate an exemplary sequence of steps that can be used to prepare a composition such as provided herein, according to some embodiments.

FIGS. 7A-7F illustrate an exemplary sequence of steps that can be used to prepare a composition such as provided herein, according to some embodiments.

FIGS. 8A-8B illustrate nonlimiting examples of compositions suitable for use in microarray analysis, according to some embodiments.

DETAILED DESCRIPTION

Figure 2A:
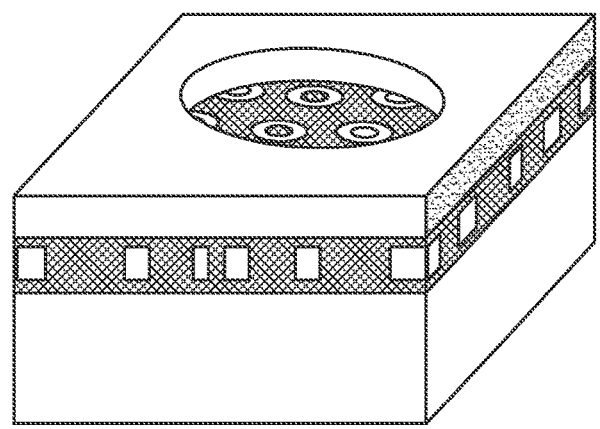
FIG. 2A schematically illustrates a perspective view of an exemplary composition including a 2D PhC superlattice in contact with an integrated microfluidic reaction chamber provided herein, FIG. 2B schematically illustrates a plan view of the composition of FIG. 2A, FIG. 2C schematically illustrates a first cross-sectional view of the composition of FIG. 2A, FIG. 2D schematically illustrates a second cross-sectional view of the composition of FIG. 2A, and FIG. 2E schematically illustrates a plot of a simulated transmission spectrum at normal incidence showing resonances of the exemplary composition of FIGS. 2A-2D provided herein.

Embodiments of the present invention provide photonic superlattice-based devices and compositions for use in luminescent imaging, and methods of using the same.

First, some exemplary terms will be defined, followed by further description of exemplary embodiments of the present photonic superlattice-based devices and compositions for use in luminescent imaging, and methods of using the same.

As used herein, the term "photonic superlattice" means a periodic structure, including one or more optically transparent materials, that selectively affects the propagation of radiation at first and second wavelengths compared to radiation at a third wavelength, wherein the third wavelength occurs between the first and second wavelengths in the electromagnetic spectrum. For example, the structure can selectively propagate radiation at the first and second wavelengths through the structure or at an angle out of the structure. For example, the structure can selectively inhibit propagation of radiation at the first and second wavelengths through the structure or at an angle out of the structure. For example, the structure can selectively propagate radiation at the third wavelength through the structure or at an angle out of the structure. For example, the structure can selectively inhibit propagation of radiation at the third wavelength through the structure or at an angle out of the structure. The material(s) can include features that are distributed in one or more dimensions, e.g., in one dimension, in two dimensions, or in three dimensions. The shape, size, and distribution of the features, as well as the refractive index of the material(s), can be tuned so as select the particular wavelengths that can propagate through or at an angle out of the photonic superlattice, and so as to select the particular wavelengths that do not propagate substantially through or at an angle out of the photonic superlattice. Illustratively, a photonic superlattice can include a material that extends in three dimensions, e.g., has a length, a width, and a thickness. The material can have two major surfaces that each lie within a plane defined by the length and the width, and separated from one another by the thickness. The material can be patterned in two or more dimensions so as to define a photonic band structure that permits propagation of at least first and second wavelengths within, or at an angle out of, the plane defined by the length and the width, and that inhibits propagation of at least a third wavelength that separates the first and second wavelengths within, or at an angle out of, the material. The pattern can include, for example, a plurality of features such as wells or posts that are defined within the material, e.g., through one or both of the major surfaces of the material, the material being absent within or between the features, such as within the wells or between the posts. A space within or between the features can be filled with one or more additional materials that respectively can have different refractive indices than that of the material and than that of one another. The particular wavelengths that propagate or do not propagate through, or at an angle out of, the photonic superlattice can be based on the refractive indices of the material and of any additional materials disposed within the features or between the features, as well as based on the characteristics of the features, such as the shape, size, and distribution of the features. The features need not all be the same as one another. For example, some of the features can differ in at least one characteristic from others of the features.

One or more of the materials of the photonic superlattice can be or include a "dielectric material," meaning a fluidic, solid, or semi-solid material that is optically transparent and is an electrical insulator. Examples of fluidic dielectric materials include gases such as air, nitrogen, and argon, as well as liquids such as water, aqueous solvents, and organic solvents. Examples of solid dielectric materials include glasses (e.g., inorganic glasses such as silica, or modified or functionalized glasses) and polymers (such as acrylics, polystyrene, copolymers of styrene and other materials, polypropylene, polyethylene, polybutene, polyurethanes, TEFLON™, cyclic olefins, polyimides, or nylon). Examples of semi-solid dielectric materials include gels, such as hydrogels. Additionally, or alternatively, one or more materials of the photonic superlattice can be or include a solid semiconductor material that is optically transparent.

As used herein, the term "gel" is intended to mean a semi-solid or semi-rigid material that is permeable to liquids and gases. Typically, gel material can swell when liquid is taken up and can contract when liquid is removed by drying. Exemplary gels can include, but are not limited to, those having a colloidal structure, such as agarose or a hydrogel; polymer mesh structure, such as gelatin; or cross-linked polymer structure, such as polyacrylamide, SFA (see, for example, US 2011/0059865, the entire contents of which are incorporated by reference herein) or PAZAM (see, for example, US 2014/0079923, the entire contents of which are incorporated by reference herein). Particularly useful gel material will conform to the shape of a well or other concave feature where it resides.

As used herein, the term "well" means a discrete concave feature in a material having a surface opening (aperture) that is completely surrounded by interstitial region(s) of the surface. A well can have characteristics such as size (e.g., volume, diameter, and depth), shape (e.g., round, elliptical, triangular, square, polygonal, star shaped (having any suitable number of vertices), irregular, or having concentric wells separated by a dielectric material), and distribution (e.g., spatial locations of the wells within the dielectric material, e.g., regularly spaced or periodic locations, or irregularly spaced or aperiodic locations). The cross section of a well can be, but need not necessarily be, uniform along the length of the well.

As used herein, the term "post" means a discrete convex feature protruding from the surface of a material and that is completely surrounded by interstitial region(s) of the surface. A post can have characteristics such as size (e.g., volume, diameter, and depth), shape (e.g., round, elliptical, triangular, square, polygonal, star shaped (having any suitable number of vertices), irregular, or having concentric posts separated by a dielectric material), and distribution (e.g., spatial locations of the posts protruding from the surface of the dielectric material, e.g., regularly spaced or periodic locations, or irregularly spaced or aperiodic locations). The cross section of a post can be, but need not necessarily be, uniform along the length of the post.

As used herein, the term "surface" means a part or layer of a material that is in contact with another material.

As used herein, the term "interstitial region" is intended to mean an area in a material or on a surface that separates areas of the material or surface. For example, an interstitial region can separate one feature of a photonic superlattice from another feature of a photonic superlattice, or an interstitial region can separate one site of an array from another site of the array.

As used herein, the term "luminescent" means emitting cold body radiation, and the term "luminophore" means an item that is luminescent. The term "luminescent" is intended to be distinct from incandescence which is radiation emitted from a material as a result of heat. Generally luminescence results when an energy source displaces an electron of an atom out of its lowest energy ground state into a higher energy excited state; then the electron returns the energy in the form of radiation so it can fall back to its ground state. A particularly useful type of luminescent item is one that emits cold body radiation when energy is provided by excitation radiation. Such items can be referred to as "photoluminescent." Examples of photoluminescent items include "fluorescent" items that emit cold body radiation relatively quickly (e.g., less than a millisecond) after excitation radiation, and "phosphorescent" items that emit cold body radiation relatively slowly (e.g., greater than or equal to a millisecond) after excitation radiation. Photoluminescence can be perceived as emission of radiation by an item at a wavelength that is a result of irradiating the item at another wavelength. Another useful type of luminescent item is one that emits cold body radiation when energy is provided by a chemical or biological reaction. Such items can be referred to as "chemiluminescent."

Any of a variety of signals can be detected in a method set forth herein including, for example, an optical signal such as absorbance of radiation, luminescence emission, luminescence lifetime, luminescence polarization, or the like; Rayleigh and/or Mie scattering; or the like. Exemplary labels that can be detected in a method set forth herein include, without limitation, a fluorophore, luminophore, chromophore, nanoparticle (e.g., gold, silver, carbon nanotubes), or the like.

As used herein the term "feature" means a distinctive and repeated variation in the structure or composition of a material such as a solid support. A collection of the features can form an array or lattice in or on the material. Exemplary features include, but are not limited to wells, posts, ridges, channels, sites bearing analytes, layers of a multilayer material, areas in or on a material having a chemical composition that differ from the chemical composition of other areas in or on the material and the like. A feature can have characteristics such as size (e.g., volume, diameter, and depth), shape (e.g., round, elliptical, triangular, square, polygonal, star shaped (having any suitable number of vertices), irregular, or having concentric features separated by a dielectric material), and distribution (e.g., spatial locations of the features within or on the dielectric material, e.g., regularly spaced or periodic locations, or irregularly spaced or aperiodic locations). The cross section of a feature can be, but need not necessarily be, uniform along the length of the feature.

As used herein, the term "site" means a location in an array for a particular species of molecule or cell (or other analyte). A site can contain only a single molecule (or cell or other analyte) or it can contain a population of several molecules (or cells or analytes) of the same species. In some embodiments, sites are present on a material prior to attaching a particular analyte. In other embodiments the site is created by attachment of a molecule or cell (or other analyte) to the material. Sites of an array are typically discrete. The discrete sites can be contiguous or they can have spaces between each other. It will be understood that a site is a type of feature. A site can function as a component of a lattice, array or both.

As used herein, the term "array" means a population of sites that can be differentiated from each other according to relative location.

As used herein, the term "pitch," when used in reference to features of a lattice (e.g. photonic superlattice) or array, is intended to refer to the center-to-center spacing for adjacent features of the lattice or array. A pattern of features can be characterized in terms of average pitch. The pattern can be ordered such that the coefficient of variation around the average pitch is small, or the pattern can be random in which case the coefficient of variation can be relatively large. In either case, the average pitch can be, for example, at least about on the order of the wavelength of light in the material. For example, average pitch can be in the range of a few nanometers to a micrometer. In particular, examples the pitch is at most 1 micrometer, 800 nm, 600 nm, 500 nm, 400 nm, 200 nm, 100 nm or smaller. Alternatively or additionally, the pitch can be at least 100 nm, 200 nm, 400 nm, 500 nm, 600 nm, 800 nm, 1 micrometer or larger. Note that in a photonic superlattice, different types of features can have different pitches and patterns than one another. For example, the pitch for the features of one type (e.g. in a first lattice) can differ from the pitch for features of another type (e.g. in a second lattice).

As used herein, the term "random" can be used to refer to the spatial distribution, e.g., arrangement, of locations on a surface. For example, one or more features of a photonic superlattice (e.g., wells or posts) can be randomly spaced such that nearest neighbor features, which can be of the same type or different type than one another, have variable spacing between each other. Alternatively, the spacing between features of the same type or a different type than one another can be ordered, for example, forming a regular pattern such as a rectilinear grid or a hexagonal grid. The present photonic superlattices can be ordered in one respect and random in another.

As used herein, the term "nucleotide" or "nucleic acid" is intended to mean a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), deoxyuridine triphosphate (dUTP), reversibly blocked adenosine triphosphate (rbATP), reversibly blocked thymidine triphosphate (rbTTP), reversibly blocked cytidine triphosphate (rbCTP), and reversibly blocked guanosine triphosphate (rbGTP). For further details on reversibly blocked nucleotide triphosphates (rbNTPs), see U.S. Patent Publication No. 2013/0079232, the entire contents of which are incorporated by reference herein.

The term "nucleotide" or "nucleic acid" also is intended to encompass any nucleotide analogue which is a type of nucleotide that includes a modified nucleobase, sugar and/or phosphate moiety. Exemplary modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. The precise sequence of nucleotides in a polynucleotide can be known or unknown. The following are exemplary examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "chemically coupled" is intended to mean an attachment between a first member and a second member. In some embodiments, such an attachment is normally irreversible under the conditions in which the attached members are used. In other embodiments, such an attachment is reversible but persists for at least the period of time in which it is used for detecting a subunit of a polymer. Such attachment can be formed via a chemical bond, e.g., via a covalent bond, hydrogen bond, ionic bond, dipole-dipole bond, London dispersion forces, or any suitable combination thereof. Covalent bonds are only one example of an attachment that suitably can be used to couple a first member to a second member. Other examples include duplexes between oligonucleotides, peptide-peptide interactions, and hapten-antibody interactions such as streptavidin-biotin, streptavidin-desthiobiotin, and digoxigenin-anti-digoxigenin. In one embodiment, an attachment can be formed by hybridizing a first polynucleotide to a second polynucleotide that inhibits detachment of the first polynucleotide from the second polynucleotide. Alternatively, an attachment can be formed using physical or biological interactions, e.g., an interaction between a first protein and a second protein that inhibits detachment of the first protein from the second protein. As used herein, a "polymerase" is intended to mean an enzyme having an active site that assembles polynucleotides by polymerizing nucleotides into polynucleotides. A polymerase can bind a primed single stranded polynucleotide template, and can sequentially add nucleotides to the growing primer to form a polynucleotide having a sequence that is complementary to that of the template.

As used herein, the term "approximately" or "about" means within 10% of the stated value.

Provided herein are compositions and devices that include photonic crystal superlattices, such as for multicolor fluorescence signal enhancement from analytes (e.g. DNA clusters) in multiple excitation and/or luminescence emission bands at normal incidence of excitation. In particular embodiments, the superlattices are compatible with previously known epifluorescence microscopy and microscope scanning systems (such as those in commercially available sequencing platforms such as produced by Illumina, Inc. (San Diego, Calif.)) that, in some circumstances, can use multiple fluorescent dyes excited at normal and imaged at normal incidence in various spectral windows. However, it should be appreciated that the present photonic superlattice-based devices, compositions, and methods suitably can be used in any type of luminescent imaging or any other suitable application, and are not limited to use in sequencing polynucleotides such as DNA.

Patterning of dielectric substrates previously has been employed successfully to control the size and uniformity of polynucleotide clusters, and to increase the density of such clusters so as to improve throughput of sequencing. See for example, US Pat. App, Publ. No. 2014/0243224 A1, which is incorporated herein by reference. However, reduction in cluster size has resulted in a considerable reduction in the amount of collected multicolor fluorescence signal. For example, detection of weak multicolor fluorescence signals from large sampling areas can become increasingly difficult as the number of labeled nucleotides in DNA clusters is reduced (e.g., down to single-molecule levels or the resolution limits of the imaging system). Significant fluorescence signal enhancement therefore can be helpful to facilitate nucleotide identification and increase the throughput of next generation SBS systems.

For example, periodic patterning of materials, such as high-index dielectrics, in the proximity of fluorescently marked biomolecules can enhance a fluorescence signal by creating one- or two-dimensional waveguides with a periodic variation of the refractive index in on the order of wavelength of light. Such waveguides, which can be referred to as photonic crystals (PhCs), photonic lattices, photonic crystal lattices, or PhC lattices, can support high-Q resonant modes that can boost fluorescent signals by resonantly enhancing fluorophore excitation, fluorescence collection, or both. For examples of use of single-color fluorescence signal enhancement using PhC lattices, see the following references, the entire contents of each of which are incorporated by reference herein: U.S. Pat. No. 7,768, 640 to Cunningham et al.; Estrada et al., "Small volume excitation and enhancement of dye fluorescence on a 2D photonic crystal surface," Opt. Express 18: 3693-3699 (2010); Zhen et al., "Enabling enhanced emission and low-threshold lasing of organic molecules using special Fano resonances of macroscopic photonic crystals," PNAS 110: 13711-13716 (2013); Kaji et al., "Fabrication of two-dimensional $Ta_2O_5$ photonic crystal slabs with ultra-low background emission toward highly sensitive fluorescence spectroscopy," Opt. Express 19: 1422-1428 (2011); and Pokhriyal et al., "Photonic crystal enhanced fluorescence using a quartz substrate to reduce limits of detection," Opt. Express 18: 24793-24808 (2010).

PhC lattices also can be used in multicolor fluorescence signal enhancement. For example, dual-excitation fluorescence signal boost has been achieved with PhCs by resonant enhancement of excitation at different wavelengths that requires adjustment of the angle of incidence of excitation source to match the resonances supported by the PhC. For further details, see U.S. Pat. No. 8,344,333 to Lu et al., the entire contents of which are incorporated by reference herein. However, because the signal enhancement scheme described in Lu et al. operates in trans-fluorescence mode by tuning the illumination angles, such a scheme is not convenient for imaging or sequencing platforms that rely on multicolor epi-illumination at a fixed angle of incidence for all wavelengths of interest, e.g., a normal, or close to normal, angle of incidence. Additionally, previously known PhC lattices (hexagonal, square or honeycomb) may not provide sufficient parameter space to align multiple resonances with the absorption and/or emission peaks of several SBS dyes.

As provided herein, photonic superlattices (which also can be referred to as superlattices, photonic crystal superlattices, or PhC superlattices) can be used for multi-wavelength operation at a fixed angle of incidence for any desired number of wavelengths of interest, as they can provide multi-wavelength resonance tuning by breaking modal degeneracies that are present in PhC lattices, and by providing additional Bragg planes for resonant feedback. For example, simple photonic lattices, including a low-loss dielectric material having a regular array of wells or depressions defined therein, can be highly symmetric and therefore can support only one or a few resonances in the visible band, where absorption and emission peaks of dyes used in fluorescence microscopy can be localized. The structural simplicity of such photonic lattices also can provide limited resonance tuning capabilities. As provided herein, increasing the complexity of the photonic lattice so as to provide a photonic superlattice, e.g., by breaking the underlying lattice periodicity can increase the number of resonances and can increase the parameter space for spectral tuning of individual resonances so as respectively to overlap with excitation wavelengths used to excite luminophores disposed within or above the photonic superlattice or so as to overlap with emission wavelengths of such luminophores disposed within or above the photonic lattice, or both, which excitation wavelengths or emission wavelengths, or both, can be at substantially the same angle as one another.

Some exemplary differences between simple PhC lattices and PhC superlattices are shown schematically in FIGS. 1A-1D. More specifically, FIG. 1A schematically illustrates plan views of square and hexagonal lattice photonic crystals (PhCs), FIG. 1B schematically illustrates plan views of exemplary compositions including PhC superlattices provided herein, FIG. 1C schematically illustrates a plot of a simulated transmission spectrum at normal incidence showing resonances of an exemplary PhC lattice, and FIG. 1D schematically illustrates a plot of a simulated transmission spectrum at normal incidence showing resonances of an exemplary composition including a PhC superlattice provided herein. The PhCs illustrated in FIG. 1A include a first material having a refractive index of $n_1$, and regular patterns of uniformly shaped and sized wells that are defined within the first material and are filled with a second material having a refractive index of $n_2$, where $n_1$ and $n_2$ are different than each other. In comparison, each of the PhC superlattices illustrated in FIG. 1B include a first material having a refractive index of $n_1$, and at least first and second pluralities of features, e.g., wells, that are defined within the first material and are filled with a second material having a refractive index of $n_2$ (where $n_1$ and $n_2$ are different than each other), wherein the first and second pluralities of features, e.g., wells, differ in at least one characteristic from one another. For example, in the various examples shown in FIG. 1B, it can be seen that some features, e.g., wells, within a given PhC superlattice can have a different size, shape, or distribution than other features, e.g., wells, within that superlattice. The first material can include first and second major surfaces (e.g., surfaces parallel to the plane shown in FIG. 1B), and the features, e.g., wells, can be defined through at least one of the first and second major surfaces. The second material, which can be disposed within, between, or over the features, e.g., wells, defined through the first and major surfaces of the first material, can include any suitable number of luminophores, e.g., one or more, two or more, three or more, four or more, or five or more luminophores, the luminescence of which can be enhanced by the spectral resonances of the PhC superlattice.

For example, PhC superlattices such as illustrated in FIG. 1B can selectively support propagation of any suitable number of wavelengths at a desired angle out of the photonic superlattice. For example, the present PhC superlattices can selectively support propagation of at least first and second wavelengths at about the same angle as one another out of the PhC superlattice, e.g., in a direction approximately normal to the first and second major surfaces of the first material, or any other suitable angle between about 0 degrees and about 90 degrees, inclusive, e.g., an angle between about 15 degrees and about 90 degrees, or between about 30 degrees and about 90 degrees, or between about 45 degrees and about 90 degrees, or between about 60 degrees and about 90 degrees, or between about 75 degrees and about 90 degrees, or between about 85 degrees and about 90 degrees. The wavelengths for which the photonic superlattice selectively supports propagation out of the superlattice at the desired angle, e.g., the first and second wavelengths, can be separated from one another by a third wavelength that does not propagate substantially at that angle out of the photonic superlattice.

For example, it can be understood that simple PhC lattices such as illustrated in FIG. 1A can include a relatively low number of resonances, e.g., one or two resonances, such as indicated by the significantly reduced emission at about 520 nm and 640 nm. In comparison, it can be understood that the present compositions including PhC superlattices such as illustrated in FIG. 1B can have numerous resonances, e.g., three or more, four or more, five or more, six or more, seven or more, or eight or more resonances, such as indicated by the multiple regions of significantly reduced emission at about 520 nm, 570 nm, 640 nm, and 700 nm in FIG. 1D. Each of such resonances can correspond to a wavelength for which the PhC superlattice selectively supports propagation out of the superlattice at or about the desired angle, and the high-transmittance regions between such resonances can correspond to non-propagating wavelengths that do not propagate substantially at the desired angle out of the superlattice. The resonances respectively can correspond to excitation wavelengths of luminophores within the second material disposed within, between, or over the features of the photonic superlattice, or to emission wavelengths of such luminophores, or any suitable combination of excitation and emission wavelengths. The excitation wavelengths all can be about at the same angle as one another, or the emission wavelengths all can be about at the same angle as one another, or both. In some embodiments in which the luminophores are disposed within or between features of the photonic superlattice, the luminophores can be excited directly by the excitation wavelengths. In some embodiments in which the luminophores are disposed over the features of the photonic superlattice, the luminophores can be disposed in the near field of the photonic superlattice and excited evanescently by the excitation wavelengths.

Superlattice design parameters can be computationally adjusted so as to tune resonances to desired excitation or emission peaks of luminophores within the second material disposed within, between, or over the features of the photonic superlattice, for example using one or more of Finite-Difference Time-Domain (FDTD), Rigorous Coupled-Wave Analysis (RCWA), and Plane-Wave Expansion (PWE). Design optimization can employ multi-parameter sweeps or self-optimization algorithms to maximize luminescence signal, e.g., fluorescence signal, in desired spectral regions. For example, the refractive indices of material(s) that a photonic superlattice is to include, and the wavelengths for which it is desired that the photonic superlattice selectively support propagation at an angle out of the superlattice, can be computationally defined, and any suitable combination of FDTD, RCWA, PWE, or any other suitable optimization program(s) can be used so as to adjust other parameters of the superlattice, such as the size, shape, and distribution of different feature types within the superlattice, so as to explore the design parameter space of the superlattice and to identify combinations of parameters that align the spectral features of the superlattice with the desired luminophore excitation or emission wavelengths. Note that the PhC superlattice can include any suitable number of differently shaped, sized, or distributed features, e.g., can include two or more pluralities of features that differ from one another in at least one characteristic, three or more pluralities of features that differ from one another in at least one characteristic, four or more pluralities of features that differ from one another in at least one characteristic, five or more pluralities of features that differ from one another in at least one characteristic, or ten or more pluralities of features that differ from one another in at least one characteristic. The features can be, but need not necessarily be, all of the same type as one another. For example, one or more features can include a well, and one or more features can include a post.

Additionally, the present compositions can include any suitable number of materials, and are not limited to including only two materials. For example, the present photonic superlattices optionally can include at least a third material having a refractive index that is different than the refractive indices of the first and second materials. The third material can be disposed over some or all of the features, e.g., over at least one of the first and second pluralities of features, and the second material can be disposed over the third material. Optionally, the third material also can be disposed over at least one of the first and second major surfaces of the first material. For example, the third material can have a higher refractive index than those of the first and second materials, and can act as a cladding so as to increase containment of light of desired wavelengths or angles within the photonic superlattice. A fourth material, which can have a different refractive index than the first, second, and optional third materials (e.g., can be a polymer or a glass), can be disposed within or between some or all of the features.

Figure 2B:
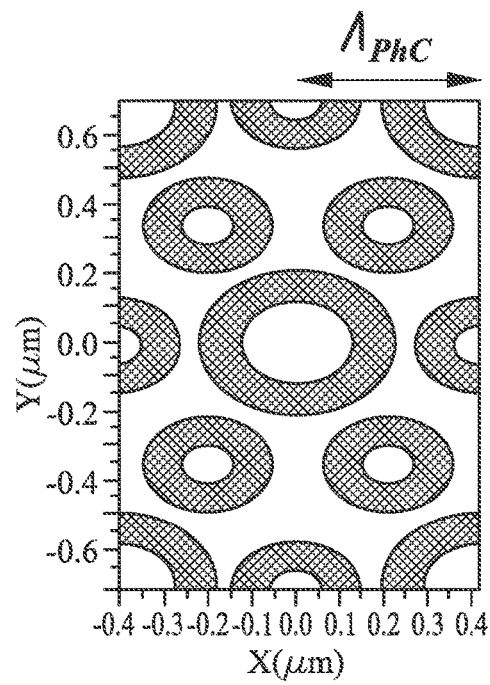
Figure 2C:
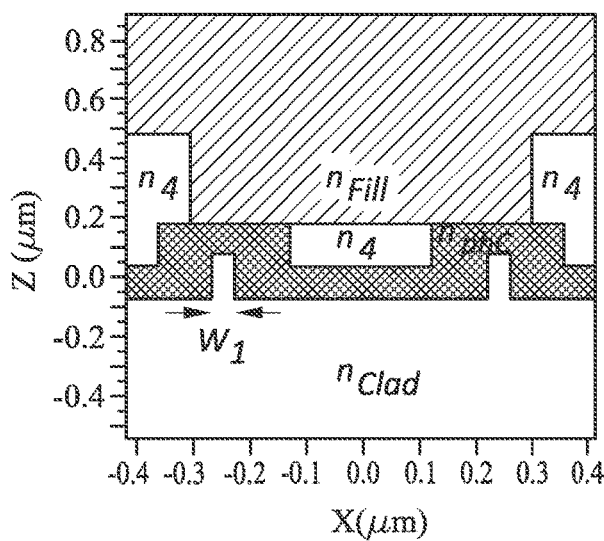
Figure 2D:
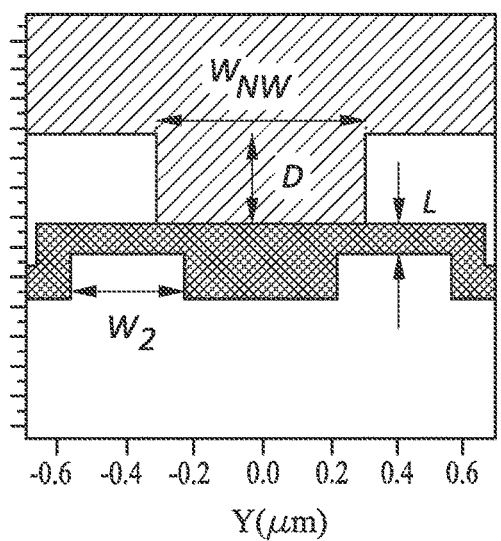
Figure 2E:
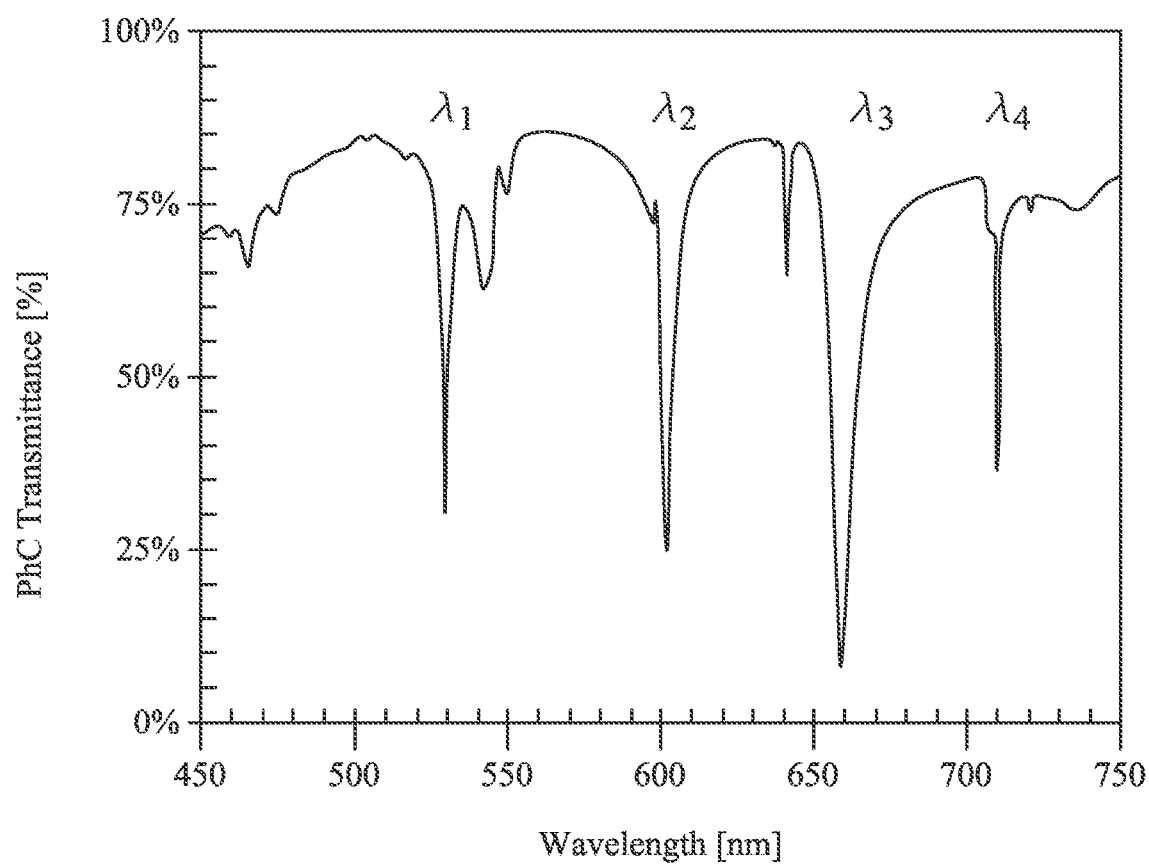

Additionally, the present superlattices can be in optical contact with one or more nucleic acids, or can be in optical contact with one or more microfluidic features, or can be in optical contact with one or more nucleic acids and one or more microfluidic features. For example, one or more nucleic acids, such as polynucleotide clusters with luminophore-labeled nucleotides, such as DNA clusters with fluorescently-labeled nucleotides, can be in optical contact with the PhC superlattice surface (e.g., disposed within the second material within, between, or over the features of the superlattice), e.g., can be localized in an array of microfluidic reaction chambers above the superlattice as shown schematically in FIGS. 2A-2D, or can be introduced to the second material within or between the features of the superlattice via such a microfluidic reaction chamber or channel. FIG. 2A schematically illustrates a perspective view of an exemplary composition including a 2D PhC superlattice in contact with an integrated microfluidic reaction chamber provided herein, FIG. 2B schematically illustrates a plan view of the composition of FIG. 2A, FIG. 2C schematically illustrates a first cross-sectional view of the composition of FIG. 2A, FIG. 2D schematically illustrates a second cross-sectional view of the composition of FIG. 2A, and FIG. 2E schematically illustrates a plot of a simulated transmission spectrum at normal incidence showing resonances of the exemplary composition of FIGS. 2A-2D provided herein.

In the exemplary composition illustrated in FIGS. 2A-2D, a photonic superlattice includes a first material ($n_1$ or $n_{clad}$) having at least first and second pluralities of features, e.g., wells, defined through a first major surface thereof, and an optional third material ($n_3$ or $n_{PhC}$) disposed over the features and the first major surface of the first material. A second material ($n_2$ or $n_{Fill}$, $n_1 \neq n_2 \neq n_3$) is disposed within, between, or over the features, e.g., over the optional third material, in a manner similar to that described above with reference to FIGS. 1A-1D. The first and second pluralities of features of the photonic superlattice can differ from one another in at least one characteristic, such as shape, size, or distribution. The present photonic superlattices optionally can be in fluidic contact with a microfluidic feature, such as a nanowell or a microfluidic channel, e.g. in a manner such as described herein with reference to FIGS. 2A-2D. For example, a fourth material ($n_4$, $n_1 \neq n_2 \neq n_3 \neq n_4$) optionally can be disposed over the third material so as to define one or more fluidic features that are disposed over the photonic crystal and within which the second material can be disposed, such as in the non-limiting example illustrated in FIGS. 2A-2D. Additionally, or alternatively, the present photonic superlattices optionally can be in contact with at least one nucleic acid, e.g. in a manner such as described herein with reference to FIGS. 2A-2D.

The composition optionally can include at least one luminophore capable of emitting luminescence at a particular wavelength. The luminescence can be collected at an angle to the first and second major surfaces of the first material, e.g., approximately normal to the first and second major surfaces. For example, in the exemplary composition illustrated in FIGS. 2A-2D, the second material can include at least first and second luminophores. In a manner similar to that described above with reference to FIGS. 1A-1D, the photonic superlattice can selectively support propagation of first and second wavelengths approximately at a defined angle out of the photonic superlattice, the first and second wavelengths being separated from one another by a third wavelength that does not selectively propagate at that defined angle out of the photonic superlattice. Conversely, the photonic superlattice can inhibit propagation of first and second wavelengths approximately at a defined angle into the photonic superlattice, the first and second wavelengths being separated from one another by a third wavelength that can propagate into the photonic superlattice. Thus, the luminescence from the first and second luminophores (i.e., at the first and second wavelengths) can be selectively collected at the defined angle out of the photonic superlattice compared to background or unwanted radiation at the third wavelength.

Optionally, the first luminophore can emit luminescence at the first wavelength, and the second luminophore can emit luminescence at the second wavelength. For example, the first luminophore can emit the first wavelength responsive to irradiation at a third wavelength, and the second luminophore can emit the second wavelength responsive to irradiation at a fourth wavelength, wherein the first, second, third, and fourth wavelengths all can be different than one another. Illustratively, the photonic superlattice can support transmission of the third and fourth (excitation) wavelengths into the photonic superlattice in such a manner that the third and fourth wavelengths can excite the first and second luminophores, resulting in the first and second luminophores respectively emitting the first and second wavelengths out of the photonic superlattice at the defined angle. Optionally, the photonic superlattice can be irradiated with the third and fourth wavelengths at an angle that can be substantially the same as the angle which the first and second wavelengths propagate out of the photonic superlattice, e.g., in a direction approximately normal to the first and second major surfaces, or can be at a different angle than that at which the first and second wavelengths propagate out of the photonic superlattice, e.g., in a direction approximately orthogonal to the first angle. Alternatively, one or both of the first and second luminophores need not be excited by radiation in order to luminesce, but instead can luminesce responsive to another suitable stimulus, such as a chemical or biological reaction. For example, one or both of the second luminophores can chemiluminesce. Additionally, or alternatively, the second material optionally can include any suitable number of luminophores, such as at least third and fourth luminophores, and the photonic superlattice can further support propagation of wavelengths respectively emitted from such luminophores, selectively, at about the defined angle out of the photonic superlattice. Such wavelengths can be separated from one another by wavelengths that are not selectively emitted at the defined angle out of the photonic superlattice.

For example, resonance wavelengths of a photonic superlattice, such as a hybrid photonic/microfluidic structure such as illustrated in FIGS. 2A-2D, can be determined at least in part by the refractive indices of the (optionally) dielectric materials included within the photonic superlattice, such as $n_{Clad}$ corresponding to the refractive index of the first material of the photonic superlattice (also referred to as $n_1$), $n_{Fill}$ corresponding to the refractive index of the second material of the photonic superlattice (also referred to as $n_2$), $n_{PhC}$ corresponding to the refractive index of the third material of the photonic superlattice (also referred to as $n_3$), the thickness of the photonic superlattice layer (L plus the height of the features of the photonic superlattice), the respective widths of features, e.g., wells, e.g., cylindrical holes) defined within the first material (e.g., $W_1$ and $W_2$, in an example having two pluralities of features that differ in the width characteristic from one another), and the lattice constant of the underlying periodic structure ($\Lambda_{PhC}$, in an example having a uniform periodicity of differently-shaped features across the superlattice). In embodiments that include such a microfluidic feature in contact with the photonic superlattice, the dimensions of such feature, e.g., $W_{NW}$ and D in embodiments including a nanowell defined in a fourth material disposed over the photonic superlattice such as illustrated in FIGS. 2A-2D, also can affect the spectral position of resonances.

In compositions in which the present photonic superlattices are in contact, e.g., optical contact, with at least one nucleic acid, at least one luminophore of the second material (disposed within, between, or over the features of the first material) optionally can be coupled to such nucleic acid. The superlattice can cause the luminophore to selectively emit luminescence at a first angle and at a wavelength, optionally responsive to radiation approximately at a second angle, where the first and second angles can be the same as or different than one another. The nucleic acid optionally can be coupled to a first polynucleotide to be sequenced, and the first polynucleotide optionally can be coupled to a feature of the photonic superlattice. The composition optionally further can include a polymerase adding the nucleic acid to a second polynucleotide that is complementary to and coupled to the first polynucleotide.

For example, in embodiments in which the second material includes first and second luminophores, the first luminophore can be coupled to the first nucleic acid, and the second luminophore can be coupled to a second nucleic acid that is different than the first nucleic acid. In compositions that further include optional additional luminophores, each such luminophore can be coupled to a respective nucleic acid. For example, a first luminophore can be coupled to a first nucleic acid, a second luminophore can be coupled to a second nucleic acid that is different than the first nucleic acid, a third luminophore can be coupled to a third nucleic acid that is different than the first and second nucleic acids, and a fourth luminophore can be coupled to a fourth nucleic acid that is different than the first, second, and third nucleic acids. For example, in compositions for use in sequencing DNA using luminescent imaging, the first luminophore can be coupled to A, the second luminophore can be coupled to G, the third luminophore can be coupled to C, and the fourth luminophore can be coupled to T. As another example, in compositions for use in sequencing RNA using luminescent imaging, the first luminophore can be coupled to A, the second luminophore can be coupled to G, the third luminophore can be coupled to C, and the fourth luminophore can be coupled to U.

In compositions including at least first and second luminophores respectively coupled to nucleic acids, the first luminophore can be coupled to a first polynucleotide to be sequenced, and the second luminophore can be coupled to a second polynucleotide to be sequenced. Illustratively, the first polynucleotide can be coupled to a feature of the first plurality of features defined within the first material, and the second polynucleotide can be coupled to a feature of the second plurality of features defined within the first material. The composition optionally further can include a first polymerase adding a first nucleic acid (to which the first luminophore is coupled) to a third polynucleotide that is complementary to and coupled to the first polynucleotide; and a second polymerase adding a second nucleic acid (to which the second luminophore is coupled) to a fourth polynucleotide that is complementary to and coupled to the second polynucleotide. The composition optionally further can include one or more fluidic or microfluidic components that facilitate sequencing of the first and second polynucleotides, such as a channel flowing a first liquid including the first and second nucleic acids and the first and second polymerases into, between, or over the first and second pluralities of features. However, it should be understood that the present compositions need not necessarily include or be in contact with a microfluidic component, such as a nanowell (reaction-chamber) such as described herein with reference to FIGS. 2A-2E. Additionally, it should be understood that the present compositions need not necessarily include or be in contact with a nucleic acid.

Compositions including photonic superlattices such as described herein, e.g., with reference to FIGS. 1A-1D and 2A-2E can include any suitable combination of optically transparent materials. Illustratively, the first material can include an optically transparent dielectric material such as a polymer or a glass, or an optically transparent semiconductor. Additionally, or alternatively, the second material can include a fluid or a gel. Additionally, or alternatively, the third material can include an optically transparent material having a different (e.g., higher) refractive index than that of the first material, such as a polymer or glass, or an optically transparent semiconductor. Additionally, or alternatively, the fourth material can include an optically transparent material having a different refractive index than that of the first, second, or third materials, such as a polymer or glass, or an optically transparent semiconductor.

Additionally, the present compositions including photonic superlattices can be prepared using any suitable combination of steps. Illustratively, a composition such as described herein with reference to FIGS. 2A-2E can be prepared using two nanoimprint lithography steps, followed by conformal dielectric deposition steps. For example, FIGS. 6A-6E illustrate an exemplary sequence of steps that can be used to prepare a composition such as provided herein. At step (a) of FIG. 6A, a first, optically transparent material such as a dielectric or a semiconductor, e.g., a polymer (such as a resin), can be disposed over a substrate, e.g., a glass substrate. At step (b) of FIG. 6B, the first material can be patterned using nanoimprint lithography, e.g., so as to define a plurality of features, such as wells or posts. At step (c) of FIG. 6C, a third, optically transparent material, e.g., a dielectric or semiconductor material having a higher refractive index than the first material, can be disposed (e.g., conformally coated) over the features defined within the first material. At step (d) of FIG. 6D, a fourth optically transparent material such as a dielectric or semiconductor, e.g., polymer (such as a resin) can be disposed over the third material. At step (e) of FIG. 6E, the fourth material can be patterned using nanoimprint lithography, e.g., so as to define a plurality of wells or nanowells. The fourth material optionally fills spaces within the photonic superlattice, such as illustrated in FIG. 6E. A second material (not specifically illustrated) that includes one or more luminophores can be disposed within the wells or nanowells, e.g., can be disposed over the photonic superlattice.

As another example, a composition such as described herein with reference to FIGS. 2A-2E can be prepared using a combination of two photolithography steps, two RIE steps, a dielectric deposition and CMP. For example, FIGS. 7A-7F illustrate another exemplary sequence of steps that can be used to prepare a composition such as provided herein. At step (a) of FIG. 7A, a first, optically transparent material such as a dielectric or a semiconductor, e.g., a polymer (such as a resin), can be disposed over a substrate, e.g., a glass substrate. At step (b) of FIG. 7B, the first material can be patterned using photolithography followed by reactive ion etch (RIE), e.g., so as to define a plurality of features, such as wells or posts. At step (c) of FIG. 7C, a third, optically transparent material, e.g., a dielectric or semiconductor material having a higher refractive index than the first material, can be disposed (e.g., conformally coated) over the features defined within the first material. At step (d) of FIG. 7D, a fourth optically transparent material such as a dielectric or semiconductor, e.g., polymer (such as a resin) can be disposed over the third material. At step (e) of FIG. 7E, the fourth material can be planarized, e.g., using chemical mechanical polishing (CMP). At step (f) of FIG. 7F, the fourth material can be patterned using photolithography followed by RIE, e.g., so as to define a plurality of wells or nanowells. The fourth material optionally fills spaces within the photonic superlattice, such as illustrated in FIG. 7F. A second material (not specifically illustrated) that includes one or more luminophores can be disposed within the wells or nanowells, e.g., can be disposed over the photonic superlattice.

Other types of compositions including photonic superlattices, and optionally also including microfluidic features, such as a nanowell (reaction-chamber) can be readily implemented for microarray analysis applications. FIGS. 8A and 8B illustrate nonlimiting examples of compositions suitable for use in microarray analysis. In the example shown in FIG. 8A, the composition can include a first material 800 within which a plurality of features are defined; a third material 802 conformally coated over the features defined in the first material; and a fourth material 804 that is interstitially disposed within the features upon which the third material is conformally coated, and also that includes a plurality of microfluidic features therein. Microarray analysis can be performed within such microfluidic features, e.g., within a second material disposed within such microfluidic features. In the example shown in FIG. 8B, the composition can include a first material 806; a fourth material 808 in which a plurality of features are defined as well as a plurality of microfluidic features; and a third material 810 that is interstitially disposed within the features of the fourth material. Microarray analysis can be performed within the microfluidic features, e.g., within a second material disposed within such microfluidic features. In another nonlimiting example, the first material included titanium pentoxide ($n_{PhC}$=2.12), the third material included a silicon dioxide cladding disposed over features of the first material ($n_{bottom\_lad}$=$n_{fill}$=1.46), and the second material disposed over the third material included water ($n_{Fill}$=1.33). The structural parameters used in RCWA simulations to generate the plot illustrated in FIG. 2E were: $\Lambda_{PhC}$=450 nm, $W_1$=50 nm, $W_2$=220 nm, L=100 nm and D=250 nm. It can be understood from FIG. 2E that the composition includes at least four resonances, at approximately 530 nm, 600 nm, 660 nm, and 710 nm.

Accordingly, the present compositions encompass PhC superlattices that support up to four, or more than four, distinct resonances (e.g., at wavelengths $\lambda_1$, $\lambda_2$, $\lambda_3$, and $\lambda_4$). Such compositions optionally can be utilized in SBS sequencing fluorescence signal enhancement at normal incidence illumination. For example, the present methods and apparatus can enhance excitation efficiency of any suitable number of luminophores using any suitable number of excitation wavelengths, e.g., can enhance excitation efficiency of four distinct excitation sources at four resonant wavelengths ($\lambda_1$, $\lambda_2$, $\lambda_3$, and $\lambda_4$) in a 4-channel SBS chemistry scheme, or can enhance excitation efficiency at two excitation wavelengths, $\lambda_1$ and $\lambda_2$, and optionally also enhancing collection efficiency at wavelengths $\lambda_3$ and $\lambda_4$, in a 2-channel SBS chemistry scheme. The present methods and apparatus can enhance collection of any suitable number of wavelengths emitted by any suitable number of luminophores, e.g., can enhance collection efficiency of four distinct emission sources (luminophores) and/or collection via four wavelength channels ($\lambda_1$, $\lambda_2$, $\lambda_3$, and $\lambda_4$) in a 4-channel SBS chemistry scheme, or can enhance collection efficiency from fewer than four distinct emission sources (luminophores) and/or via channels for two wavelengths ($\lambda_1$ and $\lambda_2$) in a 2-channel SBS chemistry scheme. Exemplary 4-channel, 3-channel, 2-channel or 1-channel SBS schemes are described, for example, in US Pat. App. Pub. No. 2013/0079232 A1 (incorporated herein by reference) and can be modified for use with the apparatus and methods set forth herein.

Figure 3A:
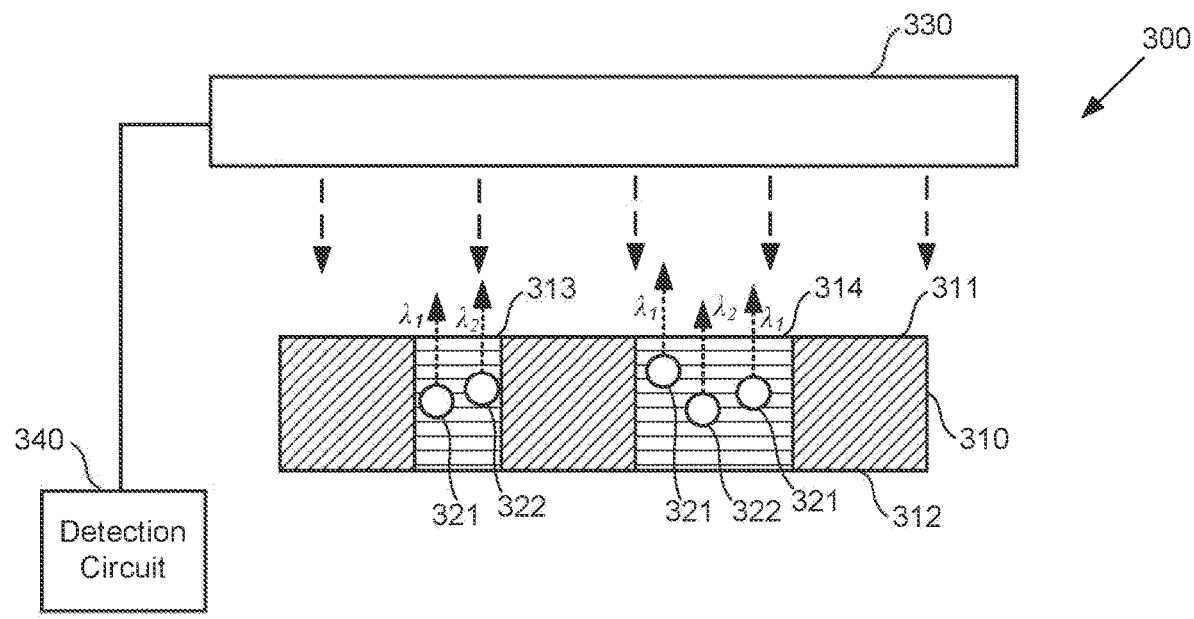
FIGS. 3A and 3B schematically illustrate cross-sectional views of exemplary photonic lattice-based devices provided herein for use in luminescent imaging.
Figure 3B:
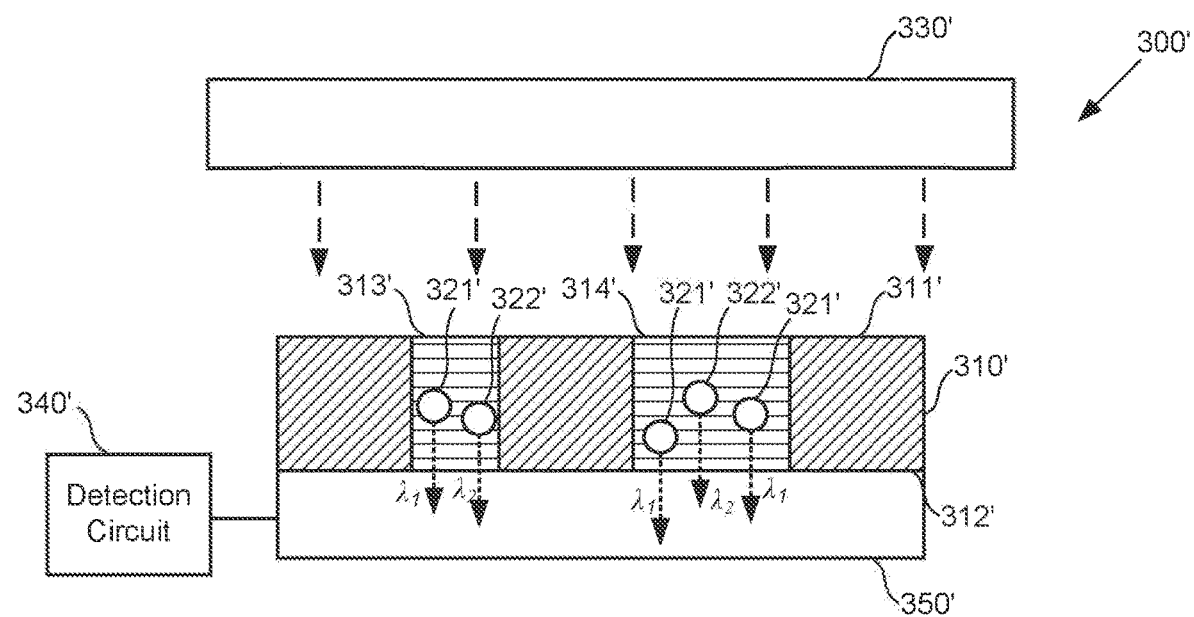

It should be understood that the present compositions suitably can be used in any of a variety of devices, e.g., for luminescent imaging. For example, FIGS. 3A and 3B schematically illustrate cross-sectional views of exemplary photonic lattice-based devices provided herein for use in luminescent imaging. FIG. 3A illustrates an exemplary device that includes photonic superlattice 310, optical component 330, and detection circuit 340. Photonic superlattice 310 includes a first material (indicated by diagonal pattern) having a first refractive index, and a second material (indicated by horizontally lined pattern) having a second refractive index that is different than the first refractive index. The first material can include first and second major surfaces 311, 312, and first and second pluralities of features, e.g., wells, 313, 314 defined through at least one of the first and second major surfaces. The features, e.g., wells, of the first plurality 313 can differ in at least one characteristic from the features, e.g., wells, of the second plurality 314, e.g., can differ in shape, size, or distribution. For example, in the exemplary photonic superlattice 310 illustrated in FIG. 3A, the features, e.g., wells, of the first plurality 313 differ in size (e.g., width) and in distribution (e.g., spacing) as compared to the features of the second plurality 314. In the nonlimiting example illustrated in FIGS. 3A and 3B, the second material can be disposed within or between the first and second pluralities of features, e.g., wells, 313, 314 and can include first and second luminophores 321, 322. For example, some of first and second luminophores 321, 322 can be located within or between the first plurality of features, e.g., wells, 313, and other of the first and second luminophores 321, 322 can be located within or between the second plurality of features, e.g., wells, 314. In other embodiments such as discussed above with reference to FIGS. 2A-2D, the second material can be disposed over the first and second pluralities of features. Illustratively, the first material can include a polymer or a glass or other suitable material, or the second material can include a fluid or a gel or other suitable material. Optionally, photonic superlattice 310 further includes a third material having a third refractive index that is different than the first and second refractive indices, the third material being disposed over at least one of the first and second pluralities of features, the second material being disposed over the third material, in a manner such as described herein with reference to FIGS. 1A-1D and 2A-2E.

Photonic superlattice 310 can selectively support propagation of a first wavelength and a second wavelength approximately at a first angle out of the photonic superlattice, e.g., first wavelength $\lambda_1$ emitted by first luminophore 321, and second wavelength $\lambda_2$ emitted by second luminophore 322. The first and second wavelengths can be separated from one another by a first non-propagating wavelength that does not selectively propagate at the first angle out of the photonic superlattice. Optical component 330 can be disposed over one of the first and second major surfaces 311, 312 of the first material, e.g., over and optionally at a spaced distance from first major surface 311. Optical component 330 can be configured so as to receive luminescence emitted by first luminophore 321 at first wavelength $\lambda_1$ approximately at the first angle, and also so as to receive luminescence emitted by second luminophore 322 at second wavelength $\lambda_2$ approximately at the first angle. In the exemplary device illustrated in FIG. 3A, the first angle is approximately normal to first major surface 311 of the first material, but it should be understood that any other angle, such as an angle disclosed herein, suitably can be used.

Optical component 330 can include an image sensor configured to image the received first and second wavelengths $\lambda_1$, $\lambda_2$. The image sensor can be spaced apart from photonic superlattice 310, or can be in contact with photonic superlattice 310, e.g., can be disposed in contact with first major surface 311. Illustratively, optical component 330 can include a complementary metal-oxide semiconductor (CMOS) based image sensor in contact with photonic superlattice 310, e.g., in a manner similar to that described below with reference to image sensor 350' of FIG. 3B. Detection circuit 340, which can be suitably electronically coupled to optical component 330, can be configured so as to receive and analyze a digital representation of the image from optical component 330. In a non-limiting example in which the first and second luminophores respectively are coupled to first and second nucleic acids, detection circuit 340 can be configured so as to identify, based on the digital representation of the image, which of the first and second nucleic acids have been to a particular polynucleotide that is coupled to the photonic superlattice, e.g., in a manner such as described herein with reference to FIGS. 2A-2E. Other detectors such as CCD cameras can be used. Exemplary detectors are set forth in Bentley et al., Nature 456:53-59 (2008), PCT Publ. Nos. WO 91/06678, WO 04/018497 or WO 07/123744; U.S. Pat. Nos. 7,057,026, 7,329,492, 7,211, 414, 7,315,019 or 7,405,281, and US Pat. App. Publ. No. 2008/0108082, each of which is incorporated herein by reference.

Additionally, in a manner similar to that set forth elsewhere herein, the second material can include any suitable number of luminophores, e.g., optionally further can include third and fourth luminophores. Photonic superlattice 310 further can selectively support propagation of a third wavelength and a fourth wavelength approximately at the first angle out of the photonic superlattice, the third and fourth wavelengths being separated from one another by a second non-propagating wavelength that does not propagate substantially at the first angle. Optical component 330 can receive luminescence emitted by the third luminophore at the third wavelength approximately at the first angle, and can receive luminescence emitted by the fourth luminophore at the fourth wavelength approximately at the first angle. Optionally, first luminophore 321 can be coupled to a first nucleic acid, second luminophore 322 can be coupled to a second nucleic acid that is different than the first nucleic acid, the third luminophore (not specifically illustrated in FIG. 3A) can be coupled to a third nucleic acid that is different than the first and second nucleic acids, and the fourth luminophore (not specifically illustrated in FIG. 3A) can be coupled to a fourth nucleic acid that is different than the first, second, and third nucleic acids.

Devices such as provided herein further can transmit radiation to the photonic superlattice so as suitably to excite luminophores therein. For example, the device further can include a broadband excitation source, such as a light emitting diode (LED), or a narrowband excitation source, such as a laser, configured to generate radiation transmitted to the photonic superlattice by an optical component that is the same as, or different than, the optical component that receives luminescence emitted by the luminophores.

For example, device 300 illustrated in FIG. 3A can include an optical component configured so as to transmit radiation (represented in FIG. 3A with the dashed-line arrows) to photonic superlattice 310 approximately at a second angle. Such optical component can be the same as optical component 330, or can be different than optical component 330. For example, optical component 330 can include a lens configured so as to receive radiation from an excitation source such as a laser or LED and to transmit such radiation at the second angle to photonic superlattice 310, such lens also being configured so as to receive luminescence emitted by luminophores of the photonic superlattice responsive to the radiation, e.g., at wavelengths $\lambda_1$ and $\lambda_2$ respectively emitted by first luminophore 321 and second luminophore 322. In another example, a separate optical component can transmit the radiation at the second angle to photonic superlattice 310, and first optical component 330 can receive the luminescence emitted responsive to same, e.g., at wavelengths $\lambda_1$ and $\lambda_2$ respectively emitted by first luminophore 321 and second luminophore 322. The second angle can be approximately the same as, or different than, the first angle. For example, FIG. 3A illustrates an exemplary configuration in which the second angle can be considered to be approximately the same as the first angle, in that the first and second angles each are approximately normal to the first and second major surfaces, although in different directions than one another. In other configurations, the second angle is different than the first angle. For example, the second angle can be approximately orthogonal to the first angle, such as in a configuration in which the second optical component is configured so as to introduce radiation into a side (minor surface) of photonic superlattice 310, and such radiation propagates through superlattice 310 in a direction parallel to first and second major surfaces 311, 312 of the superlattice so as to excite luminophores 321, 322.

In still other configurations, first optical component 330 can be disposed over first major surface 311, and the second optical component can be disposed at any suitable location within the device, e.g., over second major surface 312. For example, FIG. 3B illustrates an exemplary device 300' that includes photonic superlattice 310' that can be configured substantially as photonic superlattice 310, e.g., that includes a first material (indicated by diagonal pattern) and a second material (indicated by horizontally lined pattern) that is disposed within, between, or over first and second pluralities of features, e.g., wells, 313', 314' defined through at least one of first and second major surfaces 311', 312' of the first material, and that includes first and second luminophores 321', 322'. Device 300' optionally includes first optical component 330' disposed over first major surface 311' and configured to transmit radiation to photonic superlattice 310' at a first angle; alternatively, in configurations in which luminophores 321', 322' can luminesce without being excited by radiation, first optical component 330' can be omitted. In the configuration illustrated in FIG. 3B, second optical component 350' can be disposed over, and optionally in contact with, second major surface 312', and configured to receive luminescence emitted by luminophores 321', 322' at a second angle that can be the same as, or different than, the first angle (the first angle not being applicable in configurations omitting first optical element 330'). For example, FIG. 3B illustrates an exemplary configuration in which the second angle can be considered to be approximately the same as the first angle, in that the first and second angles each are approximately normal to the first and second major surfaces, and in the same direction as one another. In other configurations, the second angle is different than the first angle. For example, the second angle can be approximately orthogonal to the first angle, such as in a configuration in which first optical component 330' is configured so as to introduce radiation into a side (minor surface) of photonic superlattice 310', and such radiation propagates through superlattice 310' in a direction parallel to first and second major surfaces 311', 312' of the superlattice so as to excite luminophores 321', 322'.

Illustratively, second optical component 350' can include a CMOS based image sensor in contact with photonic superlattice 310'. Detection circuit 340', which can be suitably electronically coupled to second optical component 350', can be configured so as to receive and analyze a digital representation of the image from optical component 350'. In a non-limiting example in which the first and second luminophores respectively are coupled to first and second nucleic acids, detection circuit 340' can be configured so as to identify, based on the digital representation of the image, which of the first and second nucleic acids have been to a particular polynucleotide that is coupled to the photonic superlattice, e.g., in a manner such as described herein with reference to FIGS. 2A-2E.

Note that the present devices, such as devices 300 and 300' respectively illustrated in FIGS. 3A-3B, optionally can include one or more microfluidic features such as described above with reference to FIGS. 2A-2E. For example, device 300 or device 300' optionally can include at least one microfluidic feature in contact with the photonic superlattice and configured to provide a flow of one or more analytes into, between, or over the first and second pluralities of features of the photonic superlattice. Such analytes optionally can include one or more nucleic acids or one or more polymerases.

Additionally, or alternatively, the present devices can include or be in contact with one or more nucleic acids. Illustratively, first luminophore 321 or 321' can be coupled to a first polynucleotide to be sequenced, and second luminophore 322 or 322' can be coupled to a second polynucleotide to be sequenced. In a manner similar to that described above with reference to FIGS. 2A-2E, the first polynucleotide can be coupled to a feature, e.g., well, of the first plurality of features, e.g., wells, 313 or 313', and the second polynucleotide coupled to a feature, e.g., well, of the second plurality of features, e.g., wells 314 or 314'. Device 300 or device 300' optionally further can include a first polymerase adding a first nucleic acid to a third polynucleotide that is complementary to and coupled to the first polynucleotide, the first nucleic acid being coupled to first luminophore 321 or 321'; and a second polymerase adding a second nucleic acid to a fourth polynucleotide that is complementary to and coupled to the second polynucleotide, the second nucleic acid being coupled to second luminophore 322 or 322'. Device 300 or device 300' optionally further can include a channel flowing a first liquid including the first and second nucleic acids and the first and second polymerases into, between, or over the first and second pluralities of features, e.g., wells 313, 314 or 313', 314' in a manner similar to that described above with reference to FIGS. 2A-2E.

Figure 4:
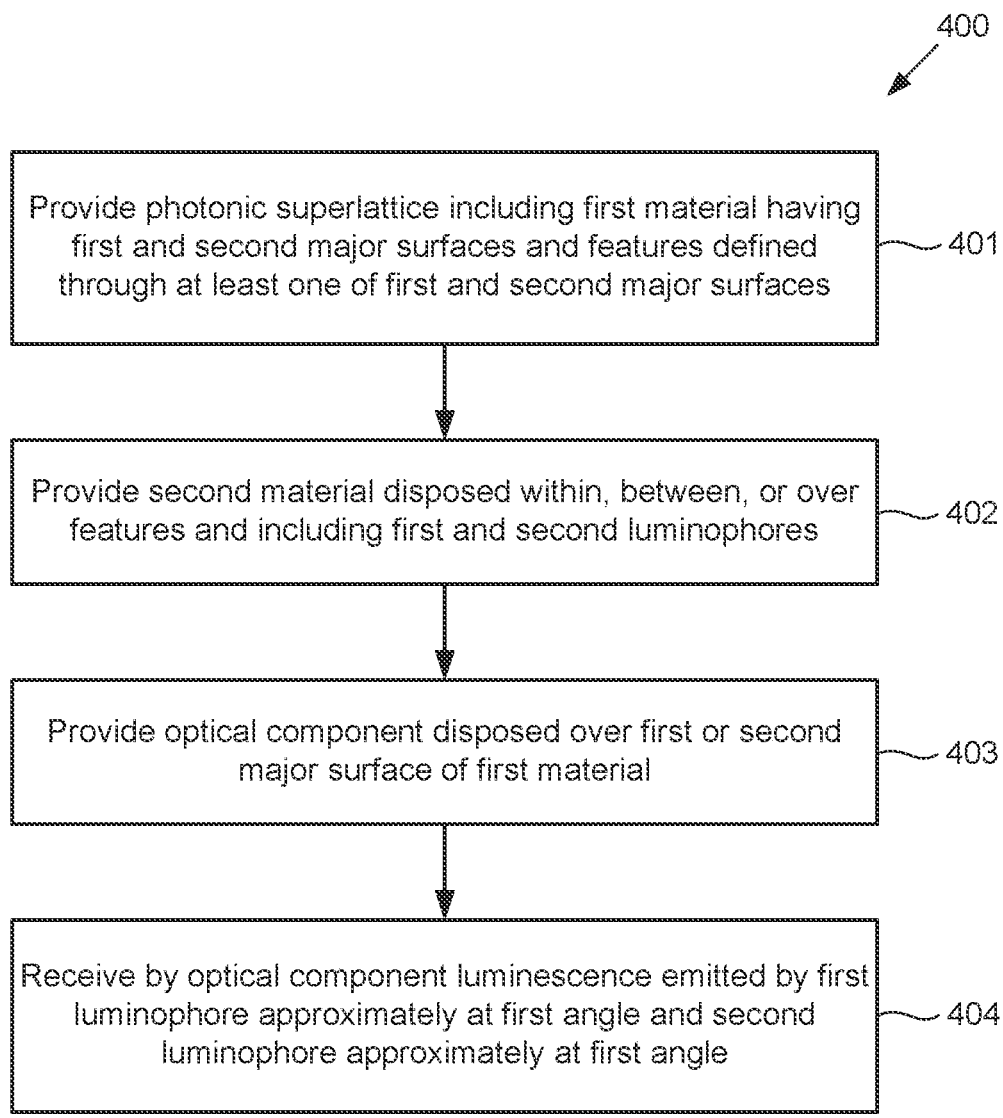
FIG. 4 illustrates an exemplary flow of steps in a method provided herein for use in luminescent imaging.

It should be understood that compositions and devices herein can be used in any suitable method for use in luminescent imaging. FIG. 4 illustrates an exemplary flow of steps in a method provided herein for use in luminescent imaging. Method 400 illustrated in FIG. 4 can include providing a photonic superlattice including a first material (401). The photonic superlattice can have any suitable configuration, e.g., such as described herein with reference to any of FIGS. 1A-1D, 2A-2E, 3A-3B, or 5A-5B. Illustratively, the first material can have a first refractive index. The first material can include first and second major surfaces and first and second pluralities of features defined through at least one of the first and second major surfaces, the features of the first plurality differing in at least one characteristic from the features of the second plurality. Optionally, the at least one characteristic includes shape, size, or distribution. The photonic superlattice can selectively support propagation of a first wavelength and a second wavelength approximately at a first angle out of the photonic superlattice, the first and second wavelengths being separated from one another by a first non-propagating wavelength that does not selectively propagate at the first angle out of the photonic superlattice, e.g., in a manner such as described herein with reference to FIGS. 1A-1D, 2A-2E, 3A-3B, and 5A-5B.

Method 400 also can include providing a second material (402). The second material can have a second refractive index that is different than the first refractive index. The second material can be disposed within, between, or over the first and second pluralities of features and can include first and second luminophores. Optionally, the first luminophore is coupled to a first nucleic acid, and the second luminophore is coupled to a second nucleic acid that is different than the first nucleic acid.

Method 400 illustrated in FIG. 4 further can include providing an optical component disposed over one of the first and second major surfaces of the first material (403). Such an optical component can have, for example, a configuration similar to that of first optical component 330 described herein with reference to FIG. 3A or second optical component 350' described herein with reference to FIG. 3B. Method 400 further can include receiving by the optical component luminescence emitted by the first luminophore at the first wavelength approximately at the first angle; and receiving by the optical component luminescence emitted by the second luminophore at the second wavelength approximately at the first angle (404), e.g., in a manner such as described herein with reference to FIGS. 3A-3B. Optionally, the first angle is approximately normal to the first and second major surfaces. Other exemplary suitable angles are described elsewhere herein.

Optionally, the photonic superlattice further can include a third material having a third refractive index that is different than the first and second refractive indices, the third material being disposed over at least one of the first and second pluralities of features, the second material being disposed over the third material, e.g., in a manner such as described herein with reference to FIGS. 1A-1D or 2A-2E.

Optionally, the second material further can include any suitable number of luminophores, such as at least third and fourth luminophores. The photonic superlattice further can selectively support propagation of a third wavelength and a fourth wavelength approximately at the first angle out of the photonic superlattice, the third and fourth wavelengths being different than each of the first and second wavelengths and being separated from one another by a second non-propagating wavelength that does not selectively propagate at the first angle, e.g., in a manner similar to that described herein with reference to FIGS. 1A-1D, 2A-2E, or 3A-3B. Method 400 optionally further can include receiving by the first optical component luminescence emitted by the third luminophore at the third wavelength approximately at the first angle; and receiving by the first optical component luminescence emitted by the fourth luminophore at the fourth wavelength approximately at the first angle. Optionally, the first luminophore can be coupled to a first nucleic acid, the second luminophore can be coupled to a second nucleic acid that is different than the first nucleic acid, the third luminophore can be coupled to a third nucleic acid that is different than the first and second nucleic acids, and the fourth luminophore can be coupled to a fourth nucleic acid that is different than the first, second, and third nucleic acids, e.g., in a manner similar to that described herein with reference to FIGS. 1A-1D, 2A-2E, or 3A-3B. Optionally, method 400 flowing one or more analytes into, between, or over the first and second pluralities of features by at least one microfluidic feature in contact with the photonic superlattice. Illustratively, such analytes optionally can include one or more nucleic acids, or one or more polymerases.

Method 400 optionally can include, by a second optical component, transmitting radiation to the photonic superlattice approximately at a second angle, the first luminophore emitting the first wavelength responsive to the radiation transmitted by the second optical component, and the second luminophore emitting the second wavelength responsive to the radiation transmitted by the second optical component. The second angle can be approximately the same as the first angle, e.g., in a manner similar to that described herein with reference to FIGS. 1A-1D, 2A-2E, or 3A-3B. Illustratively, the first and second angles each can be approximately normal to the first and second major surfaces. Alternatively, the second angle can be approximately orthogonal to the first angle. Optionally, the first and second optical components can include the same optical component, e.g., in a manner similar to that described herein with reference to FIG. 3A. Alternatively, the first optical component can be disposed over the first major surface of the first material, and the second optical component can be disposed over the second major surface of the first material, e.g., in a manner similar to that described herein with reference to FIG. 3B. Method 400 optionally can include generating by a broadband radiation source, such as an LED, the radiation transmitted to the photonic superlattice by the second optical component, e.g., in a manner similar to that described herein with reference to FIG. 3A. The first optical component optionally can include an image sensor imaging the received first and second wavelengths, e.g., in a manner such as described herein with reference to FIGS. 3A-3B.

Additionally, or alternatively, method 400 optionally further can include coupling the first luminophore to a first polynucleotide to be sequenced; and coupling the second luminophore to a second polynucleotide to be sequenced, e.g., in a manner such as described herein with reference to FIGS. 2A-2E. Optionally, method 400 further can include coupling the first polynucleotide to a feature of the first plurality of features; and coupling the second polynucleotide to a feature of the second plurality of features. Optionally, method 400 further can include by a first polymerase, adding a first nucleotide to a third polynucleotide that is complementary to and coupled to the first polynucleotide, the first nucleotide being coupled to the first luminophore; and by a second polymerase, adding a second nucleotide to a fourth polynucleotide that is complementary to and coupled to the second polynucleotide, the second nucleotide being coupled to the second luminophore. Optionally, method 400 further can include flowing a first liquid including the first and second nucleotides and the first and second polymerases into, between, or over the first and second pluralities of features.

Method 400 suitably can be adapted for use in SBS, e.g., in at least a two-channel SBS method, or a four-channel SBS method. For example, method 400 optionally can include, after receiving by the first optical component the luminescence emitted by the first and second luminophores, respectively decoupling the first and second luminophores from the first and second polynucleotides to be sequenced. For example, SBS chemistries are well known for decoupling a luminescent label, e.g., a fluorescent label, from a polynucleotide after a nucleotide coupled to that label is incorporated into the polynucleotide. Optionally, method 400 further can include, after respectively decoupling the first and second luminophores from the first and second polynucleotides to be sequenced: flowing a second liquid including third and fourth nucleotides and third and fourth polymerases into, between, or over the first and second pluralities of features, the third nucleotide being coupled to the first luminophore, the fourth nucleotide being coupled to the second luminophore; and by the third polymerase, adding the third nucleotide or the fourth nucleotide to the third polynucleotide; or by the fourth polymerase, adding the third nucleotide or the fourth nucleotide to the fourth polynucleotide.

Note that although the present photonic superlattice-based compositions, devices, and methods can include luminophores provided within a second material that is disposed within, between, or over features defined through at least one major surface of a first material, it should be appreciated that the luminophores can be provided at any suitable location relative to the photonic superlattice. For example, a composition provided herein can include a photonic superlattice, and a pattern of analyte sites in contact with the photonic superlattice. A first luminophore can be present at a first subset of analyte sites in the pattern and a second luminophore can be present at a second subset of analyte sites in the pattern. Optionally, the analyte includes nucleic acid. The photonic superlattice can be tuned to selectively propagate into the photonic superlattice a first wavelength that excites the first luminophore and a second wavelength that excites the second luminophore. The first and second wavelengths are separated by a non-propagating wavelength that does not selectively propagate into the photonic superlattice. Such compositions are provided herein, e.g., with reference to FIGS. 1A-1D, 2A-2E, 3A-3B, and 5A-5B.

Additionally, another exemplary method includes (a) providing a device that includes (i) a photonic superlattice; and (ii) a pattern of analyte sites in contact with the photonic superlattice. A first luminophore can be present at a first subset of analyte sites in the pattern and a second luminophore is present at a second subset of analyte sites in the pattern. The method also can include (b) contacting the device with radiation that includes a first wavelength and a second wavelength, wherein the photonic superlattice selectively propagates into the photonic superlattice the first wavelength to excite the first luminophore and selectively propagates into the photonic superlattice the second wavelength to excite the second luminophore. The first and second wavelengths can be separated by a non-propagating wavelength that does not selectively propagate into the photonic superlattice. The method also can include (c) detecting emission from the first and second luminophores, thereby detecting the first and second analytes. Such methods are provided herein, e.g., with reference to FIGS. 1A-1D, 2A-2E, 3A-3B, and 5A-5B.

Optionally, in such compositions and methods, the superlattice can be tuned to create field enhancements for the first and second wavelengths at the analyte sites, e.g., in a manner such as described herein with reference to FIGS. 1A-1D and 2A-2E. Optionally, a third luminophore can be present at a third subset of analyte sites in the pattern, and the photonic superlattice can be further tuned to selectively propagate into the photonic superlattice a third wavelength that excites the third luminophore, e.g., in a manner such as described herein with reference to FIGS. 1A-1D and 2A-2E. Optionally, a fourth luminophore can be present at a fourth subset of analyte sites in the pattern, and the photonic superlattice can be further tuned to selectively propagate into the photonic superlattice a fourth wavelength that excites the fourth luminophore.

The first, second, third and fourth wavelengths optionally can be separated by respective wavelengths that do not selectively propagate into the photonic superlattice.

Thus, provided herein are compositions including photonic crystal superlattices that can provide multicolor luminescence signal enhancement that can be used in luminescent imaging, e.g., are compatible with previously known epifluorescence microscopy scanning systems, such as sequencing platforms that are commercially available, e.g., from Illumina, Inc.

Note that photonic superlattice optimization for large resonant enhancement of emitted light or excitation light optionally can be based on independent tuning of multiple narrow resonances so to overlap with fixed emission or excitation wavelengths. Patterning of high-index dielectrics can increase luminescence signal, e.g., fluorescence signal, generated in the vicinity of the pattern because scattering can enhance interactions between light and luminophores, e.g., fluorophores. Signal enhancement factor potentially can decrease with the complexity of the underlying photonic lattice. As another option, rather than overlapping such narrow resonances with fixed emission or excitation wavelengths, the excitation or emission wavelengths (or both) instead can be tuned so as to overlap the resonances, e.g., by tuning laser line(s) so as to adjust the excitation wavelength(s) or by adjusting one or more properties of the luminophore(s) so as to adjust the emitted wavelength(s). As yet another option, signal enhancement can be provided using broadband excitation sources such as light emitting diodes (LEDs).

EXAMPLE

The following example is intended to be purely illustrative, and not limiting of the present invention.

Figure 5B:
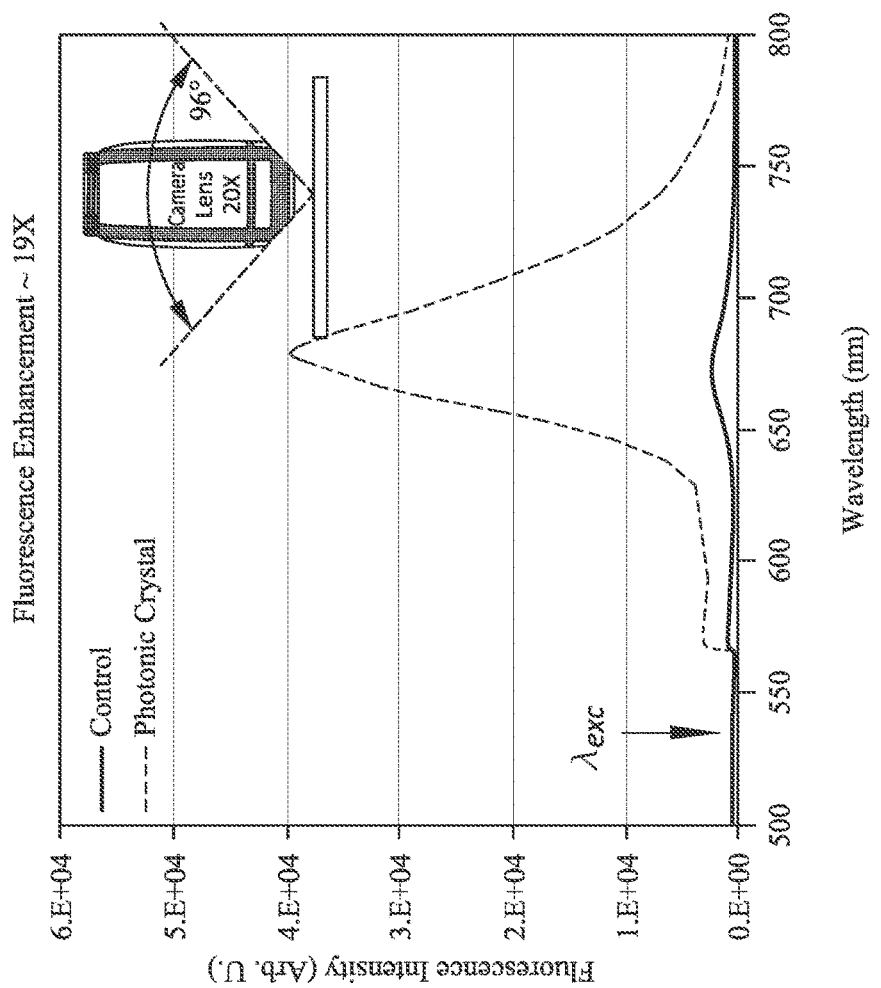
FIG. 5B schematically illustrates a plot of a collected fluorescence spectrum from the composition of FIG. 5A showing 19X signal enhancement of nanoimprinted array of nanowells coated with $Ta_2O_5$ relative to the reference, according to one example.
Figure 5A:
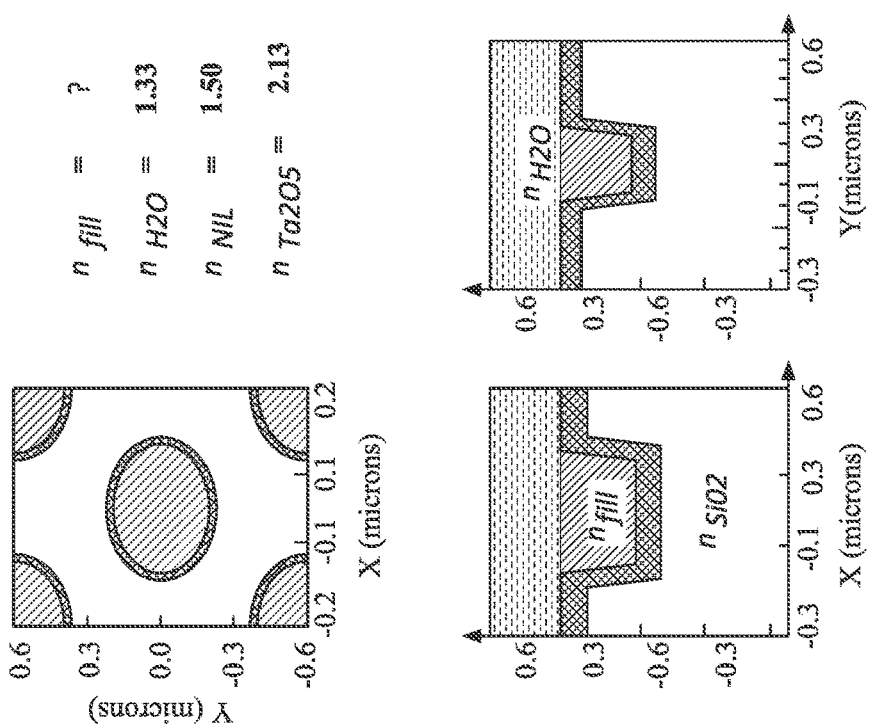
FIG. 5A schematically illustrates plan and cross-sectional views of an exemplary composition including a 2D photonic superlattice used in fluorescence signal enhancement demonstration, according to one example. Nanoimprinted resin was coated with 100 nm of tantalum pentoxide. Nanowells disposed over the photonic superlattice were filled with fluorescently stained (Cy5) hydrogel.
Figure 9:
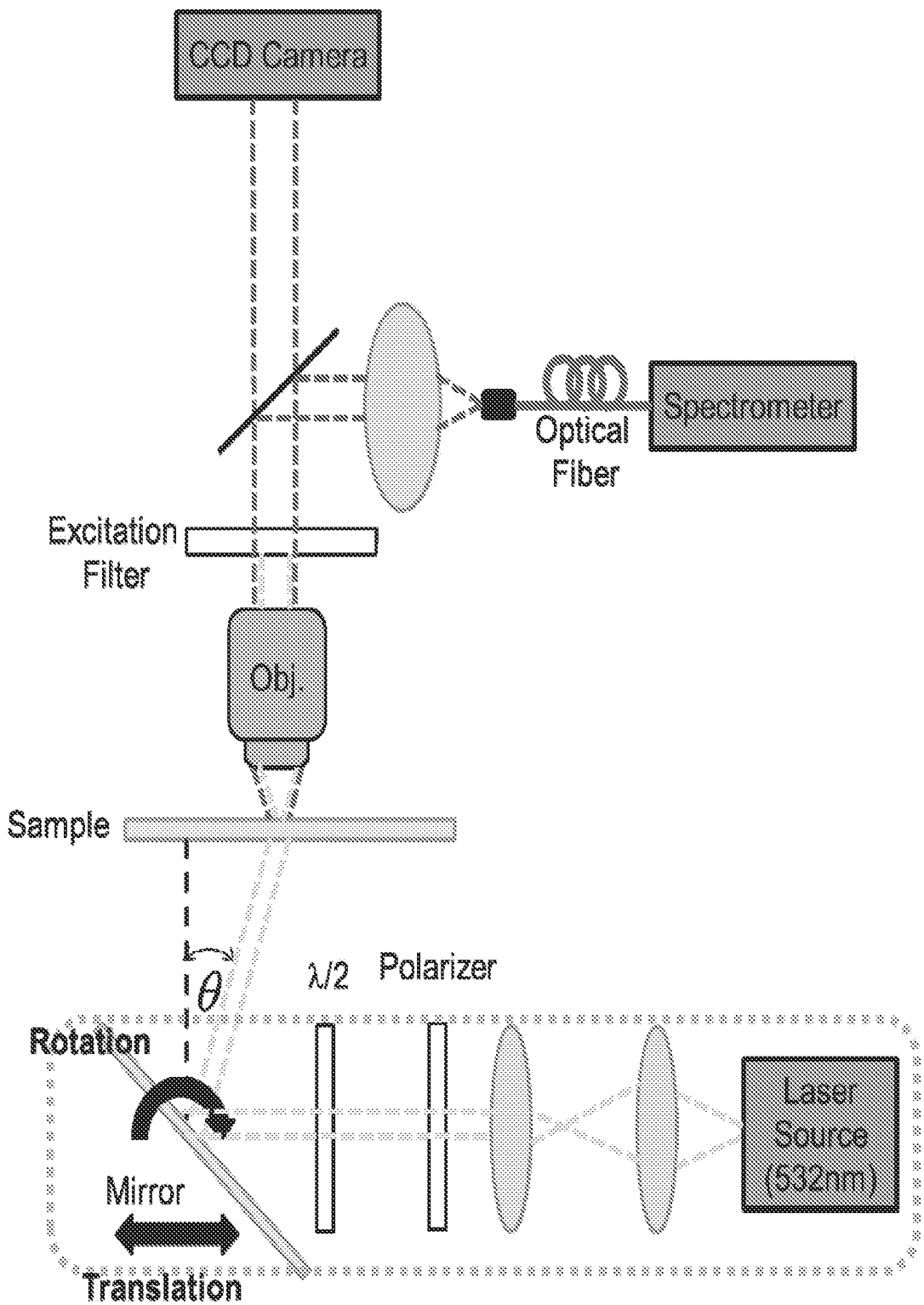
FIG. 9 schematically illustrates an exemplary experimental setup used to obtain the results illustrated in FIG. 5B.

FIG. 5A schematically illustrates plan and cross-sectional views of an exemplary composition including a 2D photonic superlattice used in fluorescence signal enhancement demonstration, according to one example. Nanoimprinted resin was coated with 100 nm of tantalum pentoxide. Nanowells were filled with fluorescently stained (Cy5) hydrogel. FIG. 5B schematically illustrates a plot of a collected fluorescence spectrum from the composition of FIG. 5A showing 19× signal enhancement of the nanoimprinted array. The fluorescence signal was collected using the experimental setup illustrated in FIG. 9 with a 0.75 NA objective, and was observed to be enhanced through a combination of excitation and collection efficiency enhancement. The experimental setup illustrated in FIG. 9 included a trans-fluorescence setup constructed to quantify signal enhancement in PhC patterned substrates, providing full control over the angle of incidence of the excitation beam; easy alignment of various fiber coupled excitation sources; imaging with a CCD camera and spectral content recognition of the collected fluorescence signal; was suitable for PhC flow-cell characterization; and allows adjustment of incidence angles ($\varphi$, $\theta$) to fine-tune monochromatic excitation source to PhC resonances. The collected fluorescence spectra with and without the vertical index confinement provided by 100 nm layer of $Ta_2O_5$ are shown in FIG. 5B. Signal enhancement was calculated by integrating the areas under the spectral curves for the two cases.

Preliminary experimental demonstration of signal enhancement such as illustrated in FIG. 5B on periodic photonic lattices defined by nanoimprint lithography (NIL) and schematically illustrated in FIG. 5A show that fluorescence signal can be enhanced by 19× at normal incidence in a broad band ranging from 630 nm to 800 nm. Accordingly, application of a PhC superlattice can broaden the spectral range where signal enhancement can be achieved as needed for a particular SBS dye system with dedicated excitation or imaging windows.

Other Alternative Embodiments

While various illustrative embodiments of the invention are described above, it will be apparent to one skilled in the art that various changes and modifications may be made therein without departing from the invention. For example, although certain compositions, systems, and methods are discussed above with reference to luminescent imaging associated with sequencing polynucleotides such as DNA or RNA, it should be understood that the present compositions, systems, and methods suitably can be adapted for use in luminescent imaging associated with any appropriate subject. The appended claims are intended to cover all such changes and modifications that fall within the true spirit and scope of the invention.

What is claimed is:

1. A device comprising:
   a periodic structure including at least first and second features each being approximately circular, the first feature having a different pitch than the second feature, the periodic structure inhibiting propagation of at least first, second, and third wavelengths; and
   a fluidic feature in contact with the periodic structure to provide a flow of analyte to the first and second features.

2. The device of claim 1, wherein the fluidic feature comprises at least one of: a microfluidic structure, a well, or a nanowell.

3. The device of claim 1, wherein the periodic structure comprises a first material having a first refractive index, and wherein the device further comprises a second material having a second refractive index that is different from the first refractive index.

4. The device of claim 3, wherein the periodic structure further comprises a third material having a third refractive index that is different from the first and second refractive indices, the third material disposed within, between, or over at least part of the periodic structure.

5. The device of claim 1, wherein the first feature is included among a first plurality of wells, wherein the second feature is included among a second plurality of wells, wherein each of the first plurality of wells has approximately a first size, and wherein each of the second plurality of wells has approximately a second size smaller than the first size.

6. The device of claim 5, wherein at least some of the first plurality of wells are positioned in a cross-shaped pattern, and wherein at least some of the second plurality of wells are positioned in corners of the cross-shaped pattern.

7. The device of claim 6, wherein the periodic structure further includes a plurality of posts, each of the plurality of posts positioned in a respective one of the first plurality of wells.

8. The device of claim 1, wherein the device is to receive first luminescence at a fourth wavelength, and to receive second luminescence at a fifth wavelength, wherein at least one of the fourth and fifth wavelengths is between two of the first, second, and third wavelengths.

9. A method comprising:
   receiving first luminescence at a first wavelength, the first luminescence received by a periodic structure including at least first and second features each being approximately circular, the first feature having a different pitch than the second feature, the periodic structure inhibiting propagation of at least second, third, and fourth wavelengths, the first wavelength being different from the second, third, and fourth wavelengths; and receiving, by the periodic structure, second luminescence at a fifth wavelength, the fifth wavelength being different from the second, third, and fourth wavelengths.

10. The method of claim 9, wherein the fifth wavelength is different from the first wavelength.

11. The method of claim 9, wherein at least one of the first and fifth wavelengths is between two of the second, third, and fourth wavelengths.

12. The method of claim 9, further comprising coupling a first luminophore to a first polynucleotide, and coupling a second luminophore to a second polynucleotide, wherein the first luminescence is emitted by the first luminophore, and wherein the second luminescence is emitted by the second luminophore.

13. The method of claim 9, wherein the first luminescence is received from a first analyte site that is in contact with the periodic structure, wherein the second luminescence is received from a second analyte site that is in contact with the periodic structure, the method further comprising tuning the periodic structure to create field enhancements for the first and fifth wavelengths at the first and second analyte sites.

14. A composition comprising:
a periodic structure including at least first and second features each being approximately circular, the first feature having a different pitch than the second feature, the periodic structure inhibiting propagation of at least first, second, and third wavelengths; and
a first material in contact with the periodic structure, the first material comprising a luminophore emitting luminescence.

15. The composition of claim 14, further comprising a pattern of analyte sites in contact with the periodic structure and with the first material.

16. The composition of claim 15, wherein the pattern of analyte sites comprises at least one of: a microfluidic structure, a well, or a nanowell.

17. The composition of claim 14, further comprising a first optical component to receive first luminescence at a fourth wavelength, and to receive second luminescence at a fifth wavelength.

18. The composition of claim 17, further comprising a second optical component to transmit radiation to the periodic structure.

19. The composition of claim 14, wherein the first feature is included among a plurality of first features, wherein at least some of the plurality of first features are positioned in a cross-shaped pattern, wherein the second feature is included among a plurality of second features, and wherein at least some of the plurality of second features are positioned in corners of the cross-shaped pattern.

20. The composition of claim 19, further comprising a plurality of posts, each of the plurality of posts positioned in a respective one of the plurality of first features.

* * * * *